United States Patent
Overbeek et al.

(10) Patent No.: US 12,378,190 B2
(45) Date of Patent: *Aug. 5, 2025

(54) TWO-COMPONENT COATING SYSTEM

(71) Applicant: COVESTRO (NETHERLANDS) B.V., Geleen (NL)

(72) Inventors: Gerardus Cornelis Overbeek, Geleen (NL); Patrick Johannes Maria Stals, Geleen (NL); Daan Van Der Zwaag, Geleen (NL); Alfred Jean Paul Bückmann, Geleen (NL)

(73) Assignee: Covestro (Netherlands) B.V., Geleen (NL)

( * ) Notice: Subject to any disclaimer, the term of this patent is extended or adjusted under 35 U.S.C. 154(b) by 614 days.

This patent is subject to a terminal disclaimer.

(21) Appl. No.: 17/792,098

(22) PCT Filed: Jan. 21, 2021

(86) PCT No.: PCT/EP2021/051388
§ 371 (c)(1),
(2) Date: Jul. 11, 2022

(87) PCT Pub. No.: WO2021/148566
PCT Pub. Date: Jul. 29, 2021

(65) Prior Publication Data
US 2023/0069357 A1    Mar. 2, 2023

(30) Foreign Application Priority Data

| | | |
|---|---|---|
| Jan. 22, 2020 | (EP) | 20153154 |
| Jan. 22, 2020 | (EP) | 20153159 |
| Jan. 22, 2020 | (EP) | 20153239 |
| Jan. 22, 2020 | (EP) | 20153240 |
| Jan. 22, 2020 | (EP) | 20153242 |
| Jan. 22, 2020 | (EP) | 20153245 |
| Jan. 22, 2020 | (EP) | 20153246 |
| Jan. 22, 2020 | (EP) | 20153249 |
| Jan. 22, 2020 | (EP) | 20153250 |
| Jan. 22, 2020 | (EP) | 20153251 |
| Jan. 22, 2020 | (EP) | 20153253 |
| Jan. 24, 2020 | (EP) | 20153628 |
| Jan. 24, 2020 | (EP) | 20153630 |
| Jul. 24, 2020 | (EP) | 20187717 |

(51) Int. Cl.
*C07D 203/10* (2006.01)
*C07D 251/32* (2006.01)
(Continued)

(52) U.S. Cl.
CPC ......... *C07D 203/10* (2013.01); *C07D 251/32* (2013.01); *C07D 403/12* (2013.01);
(Continued)

(58) Field of Classification Search
CPC .. C07D 203/10; C07D 251/32; C07D 403/12; C07D 403/14; C07D 413/14; C07D 487/14; C08F 220/1804; C08G 18/027; C08G 18/0823; C08G 18/0866; C08G 18/12; C08G 18/282; C08G 18/2825; C08G 18/283; C08G 18/2865; C08G 18/2875; C08G 18/302; C08G 18/3228; C08G 18/3231; C08G 18/3275; C08G 18/348; C08G 18/3842; C08G 18/4291; C08G 18/44; C08G 18/4808; C08G 18/4825; C08G 18/4854; C08G 18/4862; C08G 18/4879; C08G 18/6692; C08G 18/6715;
(Continued)

(56) References Cited

U.S. PATENT DOCUMENTS

| | | |
|---|---|---|
| 3,329,674 A | 7/1967 | Bulbenko et al. |
| 3,337,533 A | 8/1967 | Ham |

(Continued)

FOREIGN PATENT DOCUMENTS

| | | |
|---|---|---|
| CN | 108084870 | 5/2018 |
| EP | 0 507 407 | 10/1992 |

(Continued)

OTHER PUBLICATIONS

International Search Report dated May 18, 2021, for PCT/EP2021/051388, 4 pp.
(Continued)

*Primary Examiner* — Heidi R Kelley
*Assistant Examiner* — Adam J Berro
(74) *Attorney, Agent, or Firm* — The Webb Law Firm

(57) ABSTRACT

The present invention relates to a two-component coating system comprising a first component and a second component each of which is separate and distinct from each other, wherein the first component comprises a carboxylic acid functional polymer dissolved and/or dispersed in an aqueous medium, and the second component comprises a multi-aziridine compound having: a) from 2 to 6 of the following structural units (A): b) whereby m is an integer from 1 to 8; and R' and R" are both H b) one or more linking chains wherein each one of these linking chains links two of the structural units A; c) one or more connecting groups whereby each one of the connecting groups connects two of the structural units A; and d) a molecular weight in the range from 840 Daltons to 5000 Daltons, wherein the molecular weight is measured using MALDI-TOF mass spectrometry.

19 Claims, No Drawings

(51) Int. Cl.

| | | |
|---|---|---|
| C07D 403/12 | (2006.01) | |
| C07D 403/14 | (2006.01) | |
| C07D 413/14 | (2006.01) | |
| C07D 487/14 | (2006.01) | |
| C08F 220/18 | (2006.01) | |
| C08G 18/02 | (2006.01) | |
| C08G 18/08 | (2006.01) | |
| C08G 18/12 | (2006.01) | |
| C08G 18/22 | (2006.01) | |
| C08G 18/24 | (2006.01) | |
| C08G 18/28 | (2006.01) | |
| C08G 18/30 | (2006.01) | |
| C08G 18/32 | (2006.01) | |
| C08G 18/34 | (2006.01) | |
| C08G 18/38 | (2006.01) | |
| C08G 18/42 | (2006.01) | |
| C08G 18/44 | (2006.01) | |
| C08G 18/48 | (2006.01) | |
| C08G 18/66 | (2006.01) | |
| C08G 18/67 | (2006.01) | |
| C08G 18/73 | (2006.01) | |
| C08G 18/75 | (2006.01) | |
| C08G 18/76 | (2006.01) | |
| C08G 18/79 | (2006.01) | |
| C08G 18/83 | (2006.01) | |
| C08K 5/3412 | (2006.01) | |
| C08K 5/3492 | (2006.01) | |
| C08L 63/00 | (2006.01) | |
| C09D 7/20 | (2018.01) | |
| C09D 7/45 | (2018.01) | |
| C09D 7/63 | (2018.01) | |
| C09D 7/65 | (2018.01) | |
| C09D 11/101 | (2014.01) | |
| C09D 133/02 | (2006.01) | |
| C09D 133/04 | (2006.01) | |
| C09D 175/04 | (2006.01) | |
| C09D 175/08 | (2006.01) | |
| C09D 175/12 | (2006.01) | |

(52) U.S. Cl.
CPC ......... *C07D 403/14* (2013.01); *C07D 413/14* (2013.01); *C07D 487/14* (2013.01); *C08F 220/1804* (2020.02); *C08G 18/027* (2013.01); *C08G 18/0823* (2013.01); *C08G 18/0866* (2013.01); *C08G 18/12* (2013.01); *C08G 18/227* (2013.01); *C08G 18/246* (2013.01); *C08G 18/282* (2013.01); *C08G 18/2825* (2013.01); *C08G 18/283* (2013.01); *C08G 18/2865* (2013.01); *C08G 18/2875* (2013.01); *C08G 18/302* (2013.01); *C08G 18/3228* (2013.01); *C08G 18/3231* (2013.01); *C08G 18/3275* (2013.01); *C08G 18/348* (2013.01); *C08G 18/3842* (2013.01); *C08G 18/4291* (2013.01); *C08G 18/44* (2013.01); *C08G 18/4808* (2013.01); *C08G 18/4825* (2013.01); *C08G 18/4854* (2013.01); *C08G 18/4862* (2013.01); *C08G 18/4879* (2013.01); *C08G 18/6692* (2013.01); *C08G 18/6715* (2013.01); *C08G 18/73* (2013.01); *C08G 18/755* (2013.01); *C08G 18/758* (2013.01); *C08G 18/765* (2013.01); *C08G 18/792* (2013.01); *C08G 18/798* (2013.01); *C08G 18/833* (2013.01); *C08K 5/3412* (2013.01); *C08K 5/34924* (2013.01); *C08K 5/34926* (2013.01); *C08L 63/00* (2013.01); *C09D 7/20* (2018.01); *C09D 7/45* (2018.01); *C09D 7/63* (2018.01); *C09D 7/65* (2018.01); *C09D 11/101* (2013.01); *C09D 133/02* (2013.01); *C09D 133/04* (2013.01); *C09D 175/04* (2013.01); *C09D 175/08* (2013.01); *C09D 175/12* (2013.01); *C08G 2150/00* (2013.01)

(58) Field of Classification Search
CPC .... C08G 18/73; C08G 18/755; C08G 18/758; C08G 18/765; C08G 18/792; C08G 18/798; C08G 18/833; C08G 2150/00; C08K 5/3412; C08K 5/34924; C08K 5/34926; C08L 63/00; C09D 7/65; C09D 11/101; C09D 133/02; C09D 133/04; C09D 175/04; C09D 175/08; C09D 175/12

See application file for complete search history.

(56) References Cited

U.S. PATENT DOCUMENTS

| | | |
|---|---|---|
| 3,523,750 A | 8/1970 | Tesoro |
| 3,560,415 A | 2/1971 | Grogler et al. |
| 3,583,977 A | 6/1971 | Uelzmann |
| 3,763,132 A | 10/1973 | Meiser |
| 3,933,936 A | 1/1976 | Smith et al. |
| 5,106,993 A | 4/1992 | Kania |
| 5,133,997 A | 7/1992 | Maier et al. |
| 5,164,467 A | 11/1992 | Kania |
| 5,241,001 A | 8/1993 | Kania et al. |
| 5,258,481 A | 11/1993 | Hesselmans et al. |
| 5,359,005 A | 10/1994 | Kania et al. |
| 7,396,891 B2 | 7/2008 | Gray et al. |
| 8,318,855 B2 | 11/2012 | Schafheutle et al. |
| 9,695,481 B2 | 7/2017 | Van De Water et al. |
| 11,878,969 B2 * | 1/2024 | Overbeek ............ C09D 167/02 |
| 12,247,008 B2 * | 3/2025 | Stals ................. C09D 7/20 |
| 2007/0298006 A1 | 12/2007 | Tomalia et al. |
| 2008/0114096 A1 | 5/2008 | Qu et al. |
| 2015/0118501 A1 | 4/2015 | Lu et al. |
| 2017/0218110 A1 | 8/2017 | Arzt et al. |

FOREIGN PATENT DOCUMENTS

| | | |
|---|---|---|
| EP | 0 758 662 | 2/1997 |
| EP | 1 865 014 | 12/2007 |
| EP | 2 616 484 | 7/2013 |
| GB | 1344725 | 1/1974 |
| JP | 47-027971 | 8/1972 |
| JP | 51-141860 | 5/1976 |
| JP | 59-128291 | 7/1984 |
| JP | 11500152 | 1/1999 |
| JP | 2012529473 | 11/2012 |
| JP | 2015505889 | 2/2015 |
| WO | 2006/115547 | 11/2006 |
| WO | 2013/089927 | 6/2013 |
| WO | 2015/066868 | 5/2015 |
| WO | 2020/020714 | 1/2020 |

OTHER PUBLICATIONS

Written Opinion of the International Searching Authority dated May 18, 2021, for PCT/EP2021/051388, 6 pp.

Giel Hendriks et al., "The Extended ToxTracker Assay Discriminates Between Induction of DNA Damage, Oxidative Stress, and Protein Misfolding", Toxicological Sciences, vol. 150, No. 1, 2016, pp. 190-203.

Lee et al., "Preparation and characterization of acrylic pressure-sensitive adhesives based on UV and heat curing systems," International Journal of Adhesion and Adhesives, 2017, pp. 1-21, Elsevier.

(56) References Cited

OTHER PUBLICATIONS

Qingfang et al., "Study on heat resistance of polyurethane imide/organosilicon modified epoxy coatings", Aging and Application of Synthetic Materials, 2018, pp. 24-27, vol. 47, Issue 3.

* cited by examiner

TWO-COMPONENT COATING SYSTEM

This application is the U.S. national phase of International Application No. PCT/EP2021/051388 filed Jan. 21, 2021 which designated the U.S. and claims priority to EP 20153249.6 filed Jan. 22, 2020, EP 20153154.8 filed Jan. 22, 2020, EP 20153159.7 filed Jan. 22, 2020, EP 20153239.7 filed Jan. 22, 2020, EP 20153240.5 filed Jan. 22, 2020, EP 20153242.1 filed Jan. 22, 2020, EP 20153245.4 filed Jan. 22, 2020, EP 20153246.2 filed Jan. 22, 2020, EP 20153250.4 filed Jan. 22, 2020, EP 20153251.2 filed Jan. 22, 2020, EP 20153253.8 filed Jan. 22, 2020, EP 20153628.1 filed Jan. 24, 2020, EP 20153630.7 filed Jan. 24, 2020, and EP 20187717.2 filed Jul. 24, 2020, the entire contents of each of which are hereby incorporated by reference.

The present invention relates to two-component coating systems comprising a first component and a second component each of which is separate and distinct from each other, wherein the first component comprises a carboxylic acid functional polymer dissolved and/or dispersed in an aqueous medium, and the second component comprises a multi-aziridine compound, whereby the first and second component are separately stored, since the crosslinking reaction between the crosslinking agent and the polymer to be crosslinked may start immediately after mixing the crosslinking agent with the aqueous composition of polymer to be crosslinked.

Over the years, the need for coatings with improved resistances, like stain and solvent resistance, improved mechanical properties and improved adhesive strength is more and more growing. One or more of those properties can be elevated to a higher level by means of crosslinking. Many crosslink mechanisms have been studied over the years and for waterborne dispersions, the most useful ones include isocyanate crosslinking of hydroxyl functional dispersions, the reaction between carbodiimide and carboxylic acid, epoxy crosslinking and crosslinking using aziridine based crosslinkers.

U.S. Pat. No. 5,133,997 describes coating compositions comprising an aqueous dispersion of linear aliphatic urethane resins, an anionic surfactant and a crosslinking agent capable of facilitating the cure of said resin. Trimethylolpropane tris(2-methyl-1-aziridinepropionate), CAS number 64265-57-2, a polyfunctional aziridine crosslinker, is used as crosslinking agent, which is a well-known and very active for crosslinking carboxylic acid functional polymers. This crosslinker however has an unfavourable genotoxic profile. There is a need in the industry to improve the safety, health and environmental profile of adhesives, inks and coatings and also of the substances used for preparing adhesives, inks and coatings. Genotoxicity describes the property of chemical or physical agents that cause any type of DNA damage, which may not always lead to a transmittable mutation. Mutagenicity refers to the induction of permanent transmissible DNA changes (as DNA composition or chromosome structure), which are retained in somatic cell division and passed onto progeny in germ cells. Genotoxicity must not be confused with mutagenicity. All mutagens are genotoxic whereas not all genotoxic substances are mutagenic.

The object of the present invention is to provide a two-component coating system comprising a first component and a second component each of which is separate and distinct from each other, wherein the first component comprises a carboxylic acid functional polymer dissolved and/or dispersed in an aqueous medium, and the second component comprises a compound with at least two aziridinyl groups which has reduced genotoxicity compared to trimethylolpropane tris(2-methyl-1-aziridinepropionate) and with good crosslinking efficiency. Compounds with at least two aziridinyl groups are further referred herein as multi-aziridine compounds.

This object has surprisingly been achieved by providing a two-component coating system comprising a first component and a second component each of which is separate and distinct from each other, wherein
   the first component comprises a carboxylic acid functional polymer dissolved and/or dispersed, preferably dispersed, in an aqueous medium, and
   the second component comprises a multi-aziridine compound having:
   a) from 2 to 6 of the following structural units (A):

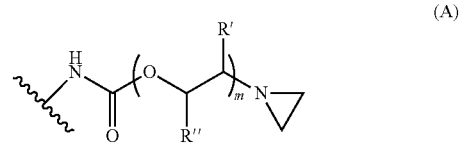

whereby
   m is an integer from 1 to 6, and
   R' and R" are both H;
   b) one or more linking chains wherein each one of these linking chains links two of the structural units A;
   c) one or more connecting groups whereby each one of these connecting groups connects two of the structural units A and whereby the connecting groups preferably consist of at least one functionality selected from: aliphatic hydrocarbon functionality, cycloaliphatic hydrocarbon functionality, aromatic hydrocarbon functionality, isocyanurate functionality, iminooxadiazinedione functionality, ether functionality, ester functionality, amide functionality, carbonate functionality, urethane functionality, urea functionality, biuret functionality, allophanate functionality, uretdione functionality and any combination thereof; and
   d) a molecular weight in the range from 840 Daltons to 5000 Daltons.

It has surprisingly been found that these multi-aziridine compounds have reduced genotoxicity compared to trimethylolpropane tris(2-methyl-1-aziridinepropionate). The multi-aziridine compounds according to the invention show either only weakly positive induced genotoxicity or even they do not show genotoxicity, i.e. they show a genotoxicity level comparable with the naturally occurring background.

The genotoxicity can be measured by the ToxTracker® assay (Toxys, Leiden, the Netherlands) as further described herein. The ToxTracker® assay can be applied for pure substances or for compositions which are the direct products obtained in the preparation of the multi-aziridine compounds of the invention. With positive induced genotoxicity is meant that the induction level of the biomarkers Bscl2-GFP and Rtkn-GFP is equal to or higher than 2-fold at at least one of 10, 25 and 50% cytotoxicity in the absence or presence of the metabolizing system rat S9 liver extract. With weakly positive induced genotoxicity is meant that the induction level of the biomarkers Bscl2-GFP and Rtkn-GFP is higher than 1.5-fold and lower than 2-fold at at least one of 10, 25 and 50% cytotoxicity (but lower than 2-fold at 10, 25 and 50% cytotoxicity) in the absence or presence of rat S9 liver extract-based metabolizing systems (aroclor1254-induced rats, Moltox, Boone, NC, USA). With genotoxicity comparable with the naturally occurring background is meant that the induction level of the biomarkers Bscl2-GFP and Rtkn-GFP is less than or equal to 1.5-fold at 10, 25 and 50% cytotoxicity in the absence and presence of rat S9 liver extract-based metabolizing systems (aroclor1254-induced rats, Moltox, Boone, NC, USA). The induction level of the genotoxicity reporters Bscl2-GFP and Rtkn-GFP is preferably less than or equal to 1.5-fold at 10, 25 and 50% cytotoxicity in the absence and presence of rat S9 liver extract-based metabolizing systems (aroclor1254-induced rats, Moltox, Boone, NC, USA). A substance showing an induction level less than or equal to 1.5-fold at 10, 25 and 50% cytotoxicity in the absence and presence of rat S9 liver extract-based metabolizing systems (aroclor1254-induced rats, Moltox, Boone, NC, USA) is not genotoxic.

U.S. Pat. No. 3,523,750 describes a process for modifying proteinaceous substrates such as wool with a multi-aziridine compound. U.S. Pat. No. 5,258,481 describes multifunctional water-dispersible crosslink agents which is an oligomeric material containing carbodiimide functionalities and reactive functional groups which are different from said carbodiimide functional group. U.S. Pat. No. 5,359,005 describes one-package coating compositions comprising at least one polymer and/or oligomer having a molecular weight of at least about 100 and bearing at least two aziridine moieties, at least two carbodiimide moieties or combinations thereof and at least one polymer and/or oligomer bearing at least two covalently blocked carboxylic acid moieties.

For all upper and/or lower boundaries of any range given herein, the boundary value is included in the range given, unless specifically indicated otherwise. Thus, when saying from x to y, means including x and y and also all intermediate values.

The term "coating composition" encompasses, in the present description, paint, coating, varnish, adhesive and ink compositions, without this list being limiting. The term "aliphatic hydrocarbon group" refers to optionally branched alkyl, alkenyl and alkynyl group. The term "cycloaliphatic hydrocarbon group" refers to cycloalkyl and cycloalkenyl group optionally substituted with at least one aliphatic hydrocarbon group. The term "aromatic hydrocarbon group" refers to a benzene ring optionally substituted with at least one aliphatic hydrocarbon group. These optional aliphatic hydrocarbon group substituents are preferably alkyl groups. Examples of cycloaliphatic hydrocarbon groups with 7 carbon atoms are cycloheptyl and methyl substituted cyclohexyl. An example of an aromatic hydrocarbon group with 7 carbon atoms is methyl substituted phenyl. Examples of aromatic hydrocarbon groups with 8 carbon atoms are xylyl and ethyl substituted phenyl.

Crosslinking efficiency of a crosslinker can be assessed by assessing the chemical resistance defined and determined as described below.

Whilst the structural units (A) present in the multi-aziridine compound present in the second component of the two-component coating system may independently have different m, R', and/or R", the structural units (A) present in the multi-aziridine compound are preferably identical to each other.

The multi-aziridine compound present in the second component of the two-component coating system is usually obtained in a composition in which, next to the multi-aziridine compound, remaining starting materials, side-products and/or solvent used in the preparation of the multi-aziridine compounds may be present. The composition may contain only one multi-aziridine compound as defined in the current invention but may also contain more than one multi-aziridine compound as defined in the current invention. Mixtures of multi-aziridine compounds are for example obtained when a mixture of polyisocyanates as starting material are used.

The urethane aziridine compound present in the second component of the two-component coating system contains from 2 to 6 of the structural units (A), preferably from 2 to 4 of the structural units (A), more preferably 2 or 3 structural units (A). m is an integer from 1 to 6, preferably m is from 1 to 4, more preferably m is 1 or 2 and most preferably m is 1.

The molecular weight of the multi-aziridine compound present in the second component of the two-component coating system is from 840 to 5000 Daltons. The molecular weight of the multi-aziridine compound present in the second component of the two-component coating system is preferably at most 3800 Daltons, more preferably at most 3600 Daltons, more preferably at most 3000 Daltons, more preferably at most 1600 Daltons, even more preferably at most 1200 Daltons. The molecular weight of the multi-aziridine compound present in the second component of the two-component coating system is preferably at least 890 Daltons, more preferably at least 940 Daltons and most preferably at least 1000 Daltons. As used herein, the molecular weight of the multi-aziridine compound is the calculated molecular weight. The calculated molecular weight is obtained by adding the atomic masses of all atoms present in the structural formula of the multi-aziridine compound. If the multi-aziridine compound is present in a composition comprising more than one multi-aziridine compound according to the invention, for example when one or more of the starting materials to prepare the multi-aziridine compound is a mixture, the molecular weight calculation can be performed for each compound individually present in the composition. The molecular weight of the multi-aziridine compound present in the second component of the two-component coating system can be measured using MALDI-TOF mass spectrometry as described in the experimental part below.

The multi-aziridine compound present in the second component of the two-component coating system comprises one or more linking chains wherein each one of these linking chains links two of the structural units A. The linking chains present in the multi-aziridine compound preferably consist of from 4 to 300 atoms, more preferably from 5 to 250, more preferably from 6 to 100 atoms and most preferably from 6 to 20 atoms. The atoms of the linking chains are preferably C and optionally N, O, S and/or P, preferably C and optionally N and/or O. The linking chains are preferably a collection of atoms covalently connected which collection of atoms consists of i) carbon atoms, ii) carbon and nitrogen atoms, or iii) carbon, oxygen and nitrogen atoms.

A linking chain is defined as the shortest chain of consecutive atoms that links two structural units A. The following drawing shows, for an example of a multi-aziridine compound according to the invention, the linking chain between two structural units A.

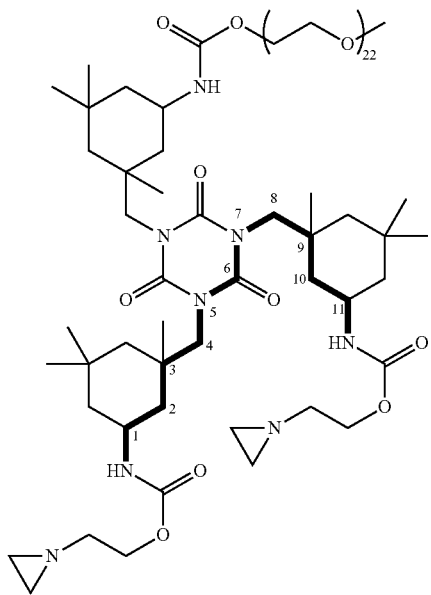

Any two of the structural units A present in the multi-aziridine compound present in the second component of the two-component coating system are linked via a linking chain as defined herein. Accordingly, each structural unit A present in the multi-aziridine compound present in the second component of the two-component coating system is linked to every other structural unit A via a linking chain as defined herein. In case the multi-aziridine compound present in the second component of the two-component coating system has two structural units A, the multi-aziridine compound has one such linking chain linking these two structural units. In case the multi-aziridine compound present in the second component of the two-component coating system has three structural units A, the multi-aziridine compound has three linking chains, whereby each of the three linking chains is linking a structural unit A with another structural unit A, i.e. a first structural unit A is linked with a second structural unit A via a linking chain and the first and second structural units A are both independently linked with a third structural unit A via their respective linking chains.

The following drawings show for an example of a multi-aziridine compound having three structural units A, the three linking chains whereby each one of the three linking chains links two structural units A.

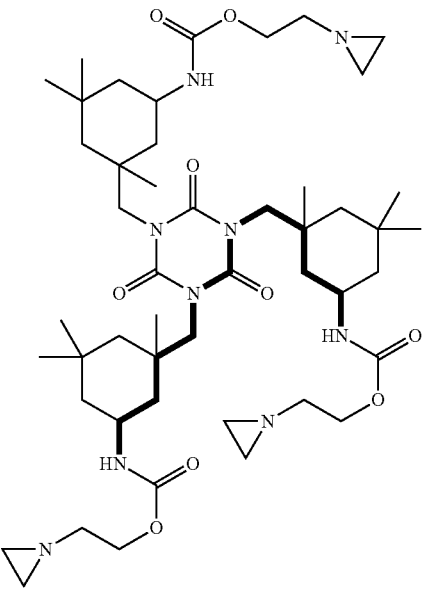

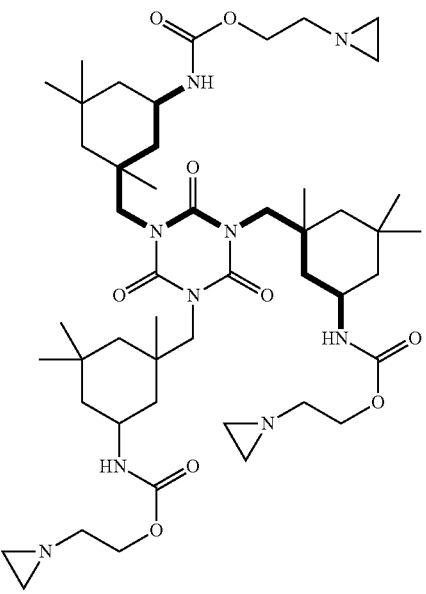

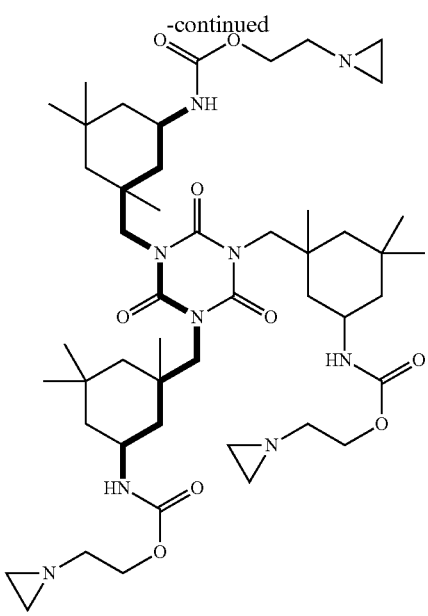

Multi-aziridine compounds present in the second component of the two-component coating system with more than two structural units A have a number of linking chains according to the following equation:

$LC = \{(AN-1) \times AN\}/2$, whereby $LC$=the number of linking chains and $AN$=the number of structural units $A$ in the multi-aziridine compound. So for example if there are 5 structural units $A$ in the multi-aziridine compound, $AN$=5; which means that there are $\{(5-1) \times 5\}/2 = 10$ linking chains.

Preferably, the number of consecutive C atoms and optionally O atoms between the N atom of the urethane group in a structural unit A and the next N atom which is either present in the linking chain or which is the N atom of the urethane group of another structural unit A is at most 9, as shown in for example the following multi-aziridine compounds according to the invention.

The multi-aziridine compound present in the second component of the two-component coating system comprises one or more connecting groups wherein each one of these connecting groups connects two of the structural units A, whereby the connecting groups preferably consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazinedione functionality, ether functionality, ester functionality, amide functionality, carbonate functionality, urethane functionality, urea functionality, biuret functionality, allophanate functionality, uretdione functionality and any combination thereof. More preferably, the connecting group is an array of consecutive functionalities, whereby each functionality is selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazinedione functionality, ether functionality, ester functionality, amide functionality, carbonate functionality, urethane functionality, urea functionality, biuret functionality, allophanate functionality, or uretdione functionality.

The following drawing shows in bold the connecting group for the following example of a multi-aziridine compound present in the second component of the two-component coating system. In this example, the connecting group connecting the two structural units A consists of the array of the following consecutive functionalities: cycloaliphatic hydrocarbon functionality 1 (a cyclic $C_9H_{16}$), aliphatic hydrocarbon functionality 2 (a $CH_2$) isocyanurate 3 (a cyclic $C_3N_3O_3$), aliphatic hydrocarbon functionality 4 (a $CH_2$) and a cycloaliphatic hydrocarbon functionality 5 (a cyclic $C_9H_{16}$) and.

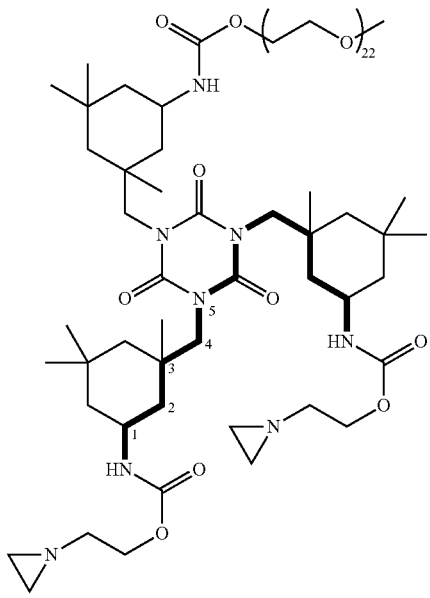

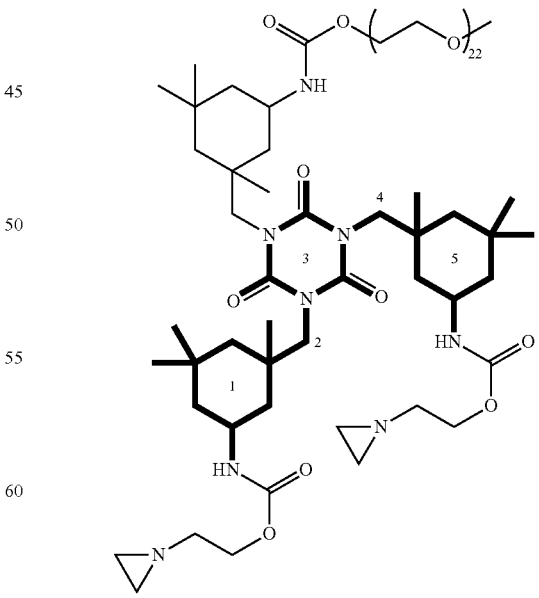

Any two of the structural units A present in the multi-aziridine compound present in the second component of the two-component coating system are preferably connected via a connecting group as defined herein. Accordingly, each structural unit A present in the multi-aziridine compound present in the second component of the two-component coating system is preferably connected to every other structural unit A with a connecting group as defined in the invention. In case the multi-aziridine compound according to the invention has two structural units A, the multi-aziridine compound has one such connecting group connecting these two structural units. In case the multi-aziridine compound according to the invention has three structural units A, the multi-aziridine compound has three such connecting groups, whereby each one of the three connecting groups is connecting a structural unit A with another structural unit A.

Preferably, the connecting groups consist of at least one functionality selected from the group consisting of aliphatic hydrocarbon functionality (preferably containing from 1 to 8 carbon atoms), cycloaliphatic hydrocarbon functionality (preferably containing from 4 to 10 carbon atoms), aromatic hydrocarbon functionality (preferably containing from 6 to 12 carbon atoms), isocyanurate functionality, iminooxadiazinedione functionality, urethane functionality, urea functionality, biuret functionality and any combination thereof. The connecting groups preferably contain an isocyanurate functionality, an iminooxadiazinedione functionality, a biuret functionality, allophanate functionality or an uretdione functionality. More preferably, the connecting groups contain an isocyanurate functionality or an iminooxadiazinedione functionality. For the sake of clarity, the multi-aziridine compound may be obtained from the reaction product of one or more suitable compound B and a hybrid isocyanurate such as for example a HDI/IPDI isocyanurate, resulting in a multi-aziridine compound with a connecting group consisting of the array of the following consecutive functionalities: a linear $C_6H_{12}$ (i.e. an aliphatic hydrocarbon functionality with 6 carbon atoms), an isocyanurate functionality (a cyclic $C_3N_3O_3$) and

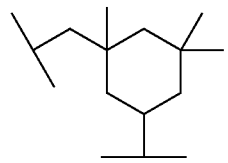 [SMILES: CC(C)CC1(C)CC(C(C)C)CC(C)(C)C1]

(i.e. a cycloaliphatic hydrocarbon functionality with 9 carbon atoms and an aliphatic hydrocarbon functionality with 1 carbon atom).

The term "aliphatic hydrocarbon functionality" refers to optionally branched alkyl, alkenyl and alkynyl groups. Whilst the optional branches of C atoms are part of the connecting group, they are not part of the linking chain. The term "cycloaliphatic hydrocarbon functionality" refers to cycloalkyl and cycloalkenyl groups optionally substituted with at least one aliphatic hydrocarbon group. Whilst the optional aliphatic hydrocarbon group substituents are part of the connecting group, they are not part of the linking chain. The optional aliphatic hydrocarbon group substituents are preferably alkyl groups. The term "aromatic hydrocarbon functionality" refers to a benzene ring optionally substituted with at least one aliphatic hydrocarbon group. The optional aliphatic hydrocarbon group substituents are preferably alkyl groups. Whilst the optional aliphatic hydrocarbon group substituents are part of the connecting group, they are not part of the linking chain.

On the connecting groups, one or more substituents may be present as pendant groups on the connection group, as shown in bold in for example the following multi-aziridine compound. These pendant groups are not part of the connecting groups.

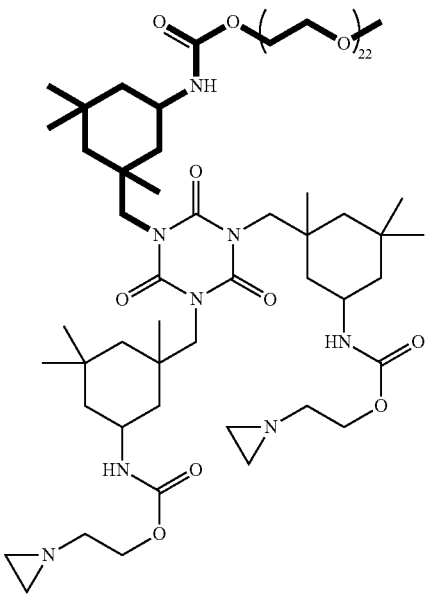

The pendant group preferably contains

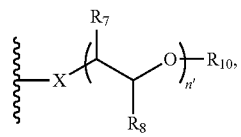

in which X, $R_7$, $R_8$, n' and $R_{10}$ are as described below. In an embodiment of the invention, the multi-aziridine compound comprises one or more connecting groups wherein each one of these connecting groups connects two of the structural units A, wherein the connecting groups consist of (i) at least two aliphatic hydrocarbon functionality or at least two cycloaliphatic hydrocarbon functionality and (ii) an isocyanurate functionality or an iminooxadiazinedione functionality, and wherein a pendant group is present on a connecting group, whereby the pendant group has the following structural formula:

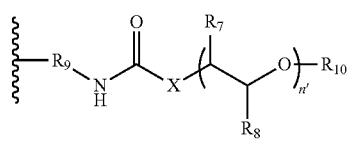

n' is the number of repeating units and is an integer from 1 to 50, preferably from 2 to 30, more preferably from 5 to 20.

X is O or NH, preferably X is O, $R_7$ and $R_8$ are independently H or $CH_3$ in each repeating unit, $R_9$ is an aliphatic hydrocarbon group, preferably containing from 1 to 8 carbon atoms, or a cycloaliphatic hydrocarbon group, preferably containing from 4 to 10 carbon atoms, and $R_{10}$ contains at most 20 carbon atoms and is an aliphatic, cycloaliphatic or aromatic hydrocarbon group or a combination thereof. In a preferred embodiment, one of $R_7$ and $R_8$ is H and the other $R_7$ or $R_8$ is $CH_3$. In another and more preferred embodiment, $R_7$ and $R_8$ are H. $R_{10}$ preferably is an aliphatic hydrocarbon group containing from 1 to 20 carbon atoms (preferably $CH_3$), a cycloaliphatic hydrocarbon group containing from 5 to 20 carbon atoms or an aromatic hydrocarbon group containing from 6 to 20 carbon atoms. The presence of the pendant group results in a decreased viscosity of the multi-aziridine compound and hence easier miscibility with the to be crosslinked polymer. In this embodiment, the multi-aziridine compound preferably contains 2 structural units A. In this embodiment the connecting group preferably consists of the array of the following consecutive functionalities: a first cycloaliphatic hydrocarbon functionality, an isocyanurate functionality or an iminooxadiazinedione functionality, and a second cycloaliphatic hydrocarbon functionality, and $R_9$ is a cycloaliphatic hydrocarbon group, whereby the first and second cycloaliphatic hydrocarbon functionality and $R_9$ are identical, more preferably the connecting group consists of the array of the following consecutive functionalities: a first aliphatic hydrocarbon functionality, an isocyanurate functionality or an iminooxadiazinedione functionality, and a second aliphatic hydrocarbon functionality, and $R_9$ is an aliphatic hydrocarbon group, whereby the first and second aliphatic hydrocarbon functionality and $R_9$ are identical.

In a preferred embodiment, the multi-aziridine compound according to the invention contains polyoxyethylene (—O—CH2-CH2-)$_x$ group(s) and/or polyoxypropylene (—O—CHCH3-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. Preferably, the multi-aziridine compound contains polyoxyethylene (—O—CH2-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. A multi-aziridine compound containing polyoxyethylene (—O—CH2-CH2-)$_x$ group(s) is preferably the reaction product of at least compound (B), a polyisocyanate and alkoxy poly(ethyleneglycol) (preferably methoxy poly(ethyleneglycol) (MPEG)) and/or poly(ethyleneglycol). The reaction product can be obtained by reacting at least compound B with the following structural formula:

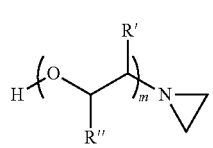

(B)

wherein R' and R" are as defined above, the polyisocyanate and alkoxy poly(ethyleneglycol) and/or poly(ethyleneglycol). The reaction product can also be obtained by reacting the polyisocyanate with alkoxy poly(ethyleneglycol) and/or poly(ethyleneglycol) and reacting the so-obtained compound with compound (B). The reaction product can also be obtained by reacting compound B with the polyisocyanate and reacting the so-obtained compound with alkoxy poly(ethyleneglycol) and/or poly(ethyleneglycol). The amount of alkoxy poly(ethyleneglycol) (preferably methoxy poly(ethyleneglycol) (MPEG)) and/or poly(ethyleneglycol) (PEG) chains with a number average molecular weight $M_n$ higher than 2200 Daltons, preferably with a $M_n$ higher than 1600 Daltons in the multi-aziridine compound as defined above is preferably less than 35 wt. %, more preferably less than 15 wt. %, more preferably less than 5 wt. % and most preferably 0 wt. %. The methoxy poly(ethyleneglycol) (MPEG) and/or poly(ethyleneglycol) (PEG) chains present in the multi-aziridine compound preferably have a $M_n$ lower than 1100 Daltons, more preferably lower than 770 Daltons and most preferably lower than 570 Daltons.

An isocyanurate functionality is defined as

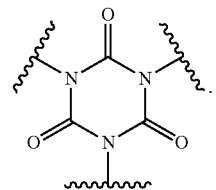 [SMILES: *n1c(=O)n(*)c(=O)n(*)c1=O]

An iminooxadiazinedione functionality is defined as

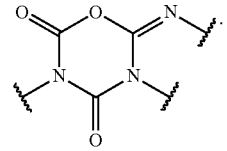

An allophanate functionality is defined as

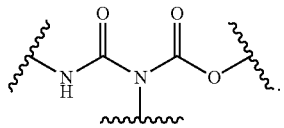 [SMILES: *NC(=O)N(*)C(=O)O*]

An uretdione functionality is defined as

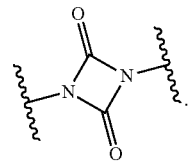 [SMILES: *N1C(=O)N(*)C1=O]

A biuret functionality is defined as

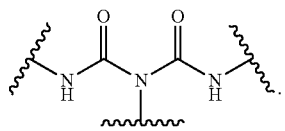 [SMILES: *NC(=O)N(*)C(=O)N*]

In a preferred embodiment of the invention, the connecting groups present in the multi-aziridine compound present in the second component of the two-component coating system consist of the following functionalities: (i) at least one aliphatic hydrocarbon functionality and/or at least one cycloaliphatic hydrocarbon functionality (ii) and an isocyanurate functionality or iminooxadiazinedione functionality or allophanate functionality or uretdione functionality and (iii) optionally at least one aromatic hydrocarbon functionality. Preferably, the connecting groups present in the multi-aziridine compound present in the second component of the two-component coating system consist of the following functionalities: (i) at least one aliphatic hydrocarbon functionality and/or at least one cycloaliphatic hydrocarbon functionality and (ii) an isocyanurate functionality or iminooxadiazinedione functionality and (iii) optionally at least one aromatic hydrocarbon functionality. A very suitable way of obtaining such multi-aziridine compound is reacting compound B with the following structural formula:

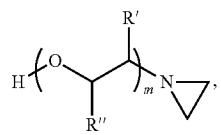

with a polyisocyanate with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Compounds based on polyisocyanate with aliphatic reactivity have a reduced tendency of yellowing over time when compared to a similar compound but based on polyisocyanate with aromatic reactivity. The term "a polyisocyanate with aromatic reactivity" being intended to mean compounds in which all of the isocyanate groups are directly bonded to a benzene or a naphthalene group, irrespective of whether aliphatic or cycloaliphatic groups are also present. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, tetramethylxylene diisocyanate TMXDI (all isomers) and higher molecular weight variants like for example their isocyanurates, or iminooxadiazinediones. More preferred polyisocyanates with aliphatic reactivity are isocyanurates or iminooxadiazinediones of 1,5-pentamethylene diisocyanate PDI, of 1,6-hexamethylene diisocyanate HDI, of isophorone diisocyanate IPDI, of 4,4'-dicyclohexyl methane diisocyanate H12MDI, of 2,2,4-trimethyl hexamethylene diisocyanate, of 2,4,4-trimethyl hexamethylene diisocyanate, of tetramethylxylene diisocyanate TMXDI. In this embodiment, preferably the connecting groups consist of the array of the following consecutive functionalities: aliphatic hydrocarbon functionality, aromatic hydrocarbon functionality and aliphatic hydrocarbon functionality (for example when using TMXDI for preparing the multi-aziridine compound) or the connecting groups consist of the array of the following consecutive functionalities: cycloaliphatic hydrocarbon functionality, aliphatic hydrocarbon functionality and cycloaliphatic hydrocarbon functionality (for example when using H12MDI for preparing the multi-aziridine compound) or more preferably, the connecting groups consist of the array of the following consecutive functionalities: aliphatic hydrocarbon functionality, isocyanurate functionality or iminooxadiazinedione functionality, and aliphatic hydrocarbon functionality. Most preferably, in this embodiment, the connecting group consists of the array of the following consecutive functionalities: aliphatic hydrocarbon functionality, isocyanurate functionality, and aliphatic hydrocarbon functionality (for example when using an isocyanurate of 1,6-hexamethylene diisocyanate and/or an isocyanurate of 1,5-pentamethylene diisocyanate for preparing the multi-aziridine compound).

The multi-aziridine compound present in the second component of the two-component coating system preferably contains at least 5 wt. %, more preferably at least 5.5. wt. %, more preferably at least 6 wt. %, more preferably at least 9 wt. %, more preferably at least 12 wt. % and preferably less than 25 wt. %, preferably less than 20 wt. % of urethane bonds. The multi-aziridine compound present in the second component of the two-component coating system preferably has an aziridine equivalent weight (molecular weight of the multi-aziridine compound divided by number of aziridinyl groups present in the multi-aziridine compound) of at least 200, more preferably at least 230 and even more preferably at least 260 Daltons and preferably at most 2500, more preferably at most 1000 and even more preferably at most 500 Daltons.

The multi-aziridine compound can be stabilized if desired with amines, preferably 0.1 to 5, more preferred 0.1 to 2.5 and most preferred 0.1 to 1 wt. % of a secondary or tertiary amine. Preferred amines include ammonia, dimethyl ethanol amine, diisopropylamine, isopropanol amine, diethyl ethanol amine, N,N-dimethyl isopropanol amine, 3-dimethylamino-1-propanol, 2-[2-(dimethylamino)ethoxy] ethanol, N-ethyl morpholine and dimethyl benzyl amine triethyl amine. Alternatively, alkali hydroxides can be used like for example NaOH, LiOH, KOH as well as combinations of amines with alkali hydroxides.

The multi-aziridine compound present in the second component of the two-component coating system is preferably obtained by reacting at least a polyisocyanate and a compound B with the following structural formula:

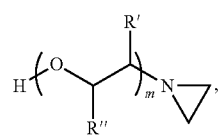

wherein R' and R" are as defined above, whereby the molar ratio of compound B to polyisocyanate is from 2 to 6, more preferably from 2 to 4 and most preferably from 2 to 3, and whereby m is defined above. Reacting the polyisocyanate with compound B may be carried out by bringing equivalent amounts of the polyisocyanate into contact with the compound B at a temperature in the range of from 0 to 110° C., more suitable from 20° C. to 110° C., more suitable from 40° C. to 95° C., even more suitable from 60 to 85° C. in the presence of for example a tin catalyst such as for example dibutyltin dilaurate or a bismuth catalyst such as for example bismuth neodecanoate. A solvent may be used, such as for example dimethylformamide DMF, acetone and/or methyl ethyl ketone. The polyisocyanate contains at least 2 isocyanate groups, preferably at least 2.5 isocyanate groups on average and more preferably at least 2.8 isocyanate groups on average. Mixtures of polyisocyanates may also be used as starting materials. Preferred polyisocyanates are polyisocyanates with aliphatic reactivity. The term "a polyisocyanate with aliphatic reactivity" being intended to mean compounds in which all of the isocyanate groups are directly bonded to aliphatic or cycloaliphatic hydrocarbon groups, irrespective of whether aromatic hydrocarbon groups are also present. The polyisocyanate with aliphatic reactivity can be a mixture of polyisocyanates with aliphatic reactivity. Preferred polyisocyanates with aliphatic reactivity are 1,5-pentamethylene diisocyanate PDI, 1,6-hexamethylene diisocyanate HDI, isophorone diisocyanate IPDI, 4,4'-dicyclohexyl methane diisocyanate H12MDI, 2,2,4-trimethyl hexamethylene diisocyanate, 2,4,4-trimethyl hexamethylene diisocyanate, p-tetra-methylxylene diisocyanate (p-TMXDI) and its meta isomer, and higher molecular weight variants like for example their isocyanurates or iminooxadiazinediones or allophanates or uretdiones. More preferred polyisocyanates with aliphatic reactivity are isocyanurates or iminooxadiazinediones of 1,5-pentamethylene diisocyanate PDI, of 1,6-hexamethylene diisocyanate HDI, of isophorone diisocyanate IPDI, of 4,4'-dicyclohexyl methane diisocyanate H12MDI, of 2,2,4-trimethyl hexamethylene diisocyanate, of 2,4,4-trimethyl hexamethylene diisocyanate, of tetramethylxylene diisocyanate TMXDI. Even more preferred polyisocyanates with aliphatic reactivity are an isocyanurate or iminooxadiazinedione of 1,6-hexamethylene diisocyanate, an isocyanurate or iminooxadiazinedione of 1,5-pentamethylene diisocyanate, an isocyanurate or iminooxadiazinedione of IPDI. A suitable HDI containing iminooxadiazinedione trimer is Desmodur® N3900, obtainable from Covestro. A suitable HDI containing allophanate is Desmodur® XP2860, obtainable from Covestro. A suitable HDI containing uretdione is Desmodur® N3400, obtainable from Covestro. Suitable HDI based isocyanurates trimers can for example be obtained from Covestro (Desmodur® N3600), Vencorex (Tolonate™ HDT LV), Asahi Kasei (Duranate™ TPA-100), Evonik (Vestanat® HT 2500/LV) and Tosoh (Coronate® HXR LV). Compound B is preferably 1-(2-hydroxyethyl)ethylenimine (CAS No. 1072-52-2).

The multi-aziridine compound present in the second component of the two-component coating system is preferably obtained in a process comprising at least the following step (i):

(i) Reacting compound B with a polyisocyanate.

The reaction (step (i)) of compound B with the polyisocyanate can be carried out, for example, by bringing equivalent amounts of the polyisocyanate into contact with the adduct at a temperature in the range of from 20° C. to 110° C., more suitable from 40° C. to 95° C. at atmospheric pressure, in the presence of for example a tin catalyst such as for example dibutyltin dilaurate.

An example of a preferred multi-aziridine compound according to the invention is

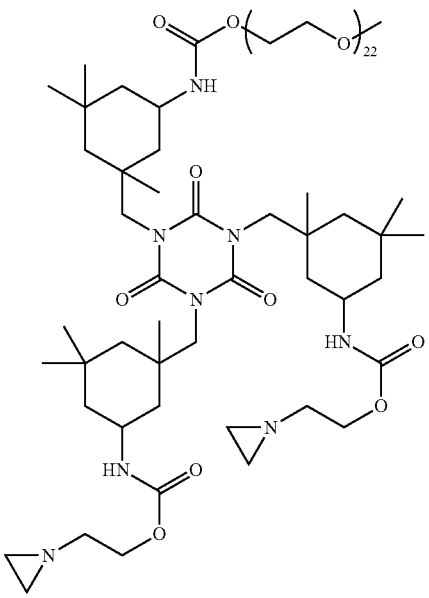

A further aspect of the current invention is a two-component coating system comprising a first component and a second component each of which is separate and distinct from each other, wherein the first component comprises a carboxylic acid functional polymer dissolved and/or dispersed, preferably dispersed, in an aqueous medium and wherein the second component is a crosslinker composition comprising at least one multi-aziridine compound as defined herein and further comprising at least one additional component, such as for example remaining starting materials, side-products and/or solvent used for preparing the multi-aziridine compound according to the invention. The crosslinker composition may contain only one multi-aziridine compound according to the invention but may also contain more than one multi-aziridine compound according to the invention. Mixtures of multi-aziridine compounds are for example obtained when a mixture of polyisocyanates as starting material to prepare the multi-aziridine are used. After having obtained the multi-aziridine compound(s), the multi-aziridine compound(s) may be separated, the reaction product may be used without further purification or solvent used for preparing the multi-aziridine compound(s) may be removed from the composition obtained in the preparation of the multi-aziridine compound(s) of the invention. The amount of multi-aziridine compounds in the crosslinker composition is usually at least 10 wt. %, usually often at least 15 wt. % and most often at least 25 wt. % relative to total amount of the composition. The amount of multi-aziridine compounds as defined in the current invention present in the crosslinker composition is preferably at least 60 wt. %, more preferably at least 80 wt. % and most preferably at least 99 wt. %, relative to total amount of the crosslinker composition. The molecular weight of the multi-aziridine compounds in the crosslinker composition is in the range of from 840 Daltons to 5000 Daltons. Preferred molecular weights are as described above and molecular weights of the multi-aziridine compounds are determined using MALDI-TOF-MS as described in the experimental part herein below. MALDI-TOF-MS means matrix-assisted laser desorption ionization time of flight mass spectroscopy.

The amount of aziridine functional molecules, present in the crosslinker composition, having a molecular weight lower than 250 Daltons, more preferably lower than 350 Daltons, even more preferably lower than 450 Daltons, even more preferably lower than 550 Daltons and even more preferably lower than 820 Daltons is preferably lower than 1.5 wt. %, more preferably lower than 1 wt. %, even more preferably lower than 0.5 wt. % and most preferably lower than 0.1 wt. %, relative to the total weight of the crosslinker composition, whereby the molecular weight is determined using LC-MS as described in the experimental part below.

The average number of aziridinyl groups with structural formula (C)

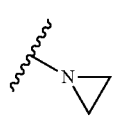

(C)

per aziridinyl-containing molecule in the crosslinker composition is preferably at least 1.8, more preferably at least 2, more preferably at least 2.2 and preferably less than 10, more preferably less than 6 and most preferably less than 4. Most preferably, the average number of aziridinyl groups per aziridinyl-containing molecule in the crosslinker composition is from 2.2 to 3. The calculated average amount of urethane bonds is at least 5 wt. %, more preferably at least 5.5. wt. %, more preferably at least 6 wt. %, more preferably at least 9 wt. %, more preferably at least 12 wt. % and preferably and less than 25 wt. %, preferably less than 20 wt. % of urethane bonds, relative to the total weight of the multi-aziridine compounds present in the crosslinker composition.

In view of the potential water sensitivity of the multi-aziridine compounds as defined herein, the crosslinker composition is preferably free of substantial amount of water and more preferably is free of water. Free of substantial amount of water means less than 15 wt. %, preferably less than 5 wt. %, more preferably less than 1 wt. % and most preferably less than 0.1 wt. %. In view of the potential water sensitivity of the multi-aziridine compounds as defined herein, water is preferably not deliberately (i.e. small amounts of water may be present in the compounds used to prepare the multi-aziridine compound(s) according to the invention) be added to the composition.

The multi-aziridine compounds according to the invention preferably have a Brookfield viscosity of at least 10000 mPa·s at 25° C., more preferably at least 20000, more preferably at least 50000 and preferably at most 1000000, more preferably at most 500000, and even more preferably at most 200000 mPa·s at 25° C. As used herein, the Brookfield viscosity is determined according to ISO 2555-89. In an alternative embodiment the viscosity of the multi-aziridine was measured with a Brookfield with spindle S63, @ 25° C. at 80% solids in dimethyl formamide (DMF). The viscosity as measured according to this method is preferably in the range of 300 to 20000 mPas, more preferably in the range of from 500 to 12000 and most preferably in the range of from 700 to 3000 mPas.

The carboxylic acid functional polymer present in the first component of the two-component coating system contains carboxylic acid groups and/or carboxylate groups which are preferably free of a covalent bond that blocks these groups to chemically react with the aziridine moiety present in the multi-aziridine compound. As used herein, the amount of carboxylic acid groups present in the carboxylic acid functional polymer is the summed amount of deprotonated and protonated carboxylic acid groups present in the polymer to be crosslinked, i.e. in the carboxylic acid functional polymer. Thus, the amount of carboxylic acid groups present in the carboxylic acid functional polymer is the summed amount of carboxylate groups and carboxylic acid groups present in the carboxylic acid functional polymer. The polymer to be crosslinked preferably comprises carboxylate groups which are at least partially neutralized with base. Preferably at least part of the base is a volatile base. Preferably, at least a part of the carboxylic acid groups present in the carboxylic acid functional polymer to be crosslinked are subjected to deprotonation to obtain carboxylate groups. The deprotonation is effected by neutralizing the carboxylic acid functional polymer with a base. Examples of suitable bases are ammonia, secondary amines, tertiary amines, LiOH, NaOH and/or KOH. Examples of secondary amines and tertiary amines are described above. Preferred bases are tertiary amines. Preferred tertiary amines are as described above. Most preferred is triethylamine. The pH of the first component is, prior to combining with the second component, preferably at least 7, more preferably at least 7.5, even more preferably at least 8 and even more preferably at least 8.5.

Non-limited examples of crosslinkable carboxylic acid functional polymers are vinyl polymers like styrene-acrylics, (meth)acrylic copolymers, vinyl acetate (co)polymers such as for example vinyl acetate vinyl chloride ethylene polymers, polyurethanes, polycondensates like polyesters, polyamides, polycarbonates and hybrids of any of these polymers where at least one of the two polymers have a carboxylic acid functionality. The carboxylic acid functional polymer is preferably selected from the group consisting of polyesters, polycarbonates, polyamides, vinyl polymers, polyacrylates, polymethacrylates, poly(acrylate-co-methacrylate)s, polyurethanes, poly(urethane-co-acrylate)s, poly(urethane-co-methacrylate)s, poly(urethane-co-acrylate-co-methacrylate), polyureas, and mixtures thereof. Preferably by vinyl polymer is meant a polymer comprising reacted residues of styrene and acrylates and/or methacrylates. In an embodiment of the invention, preferred crosslinkable carboxylic acid functional polymers are selected from the group consisting of vinyl polymers, polyacrylates, polymethacrylates, poly(acrylate-co-methacrylate)s and mixtures thereof. In another embodiment, the carboxylic acid functional polymer is selected from the group consisting of polyurethanes, poly(urethane-co-acrylate)s, poly(urethane-co-methacrylate)s, poly(urethane-co-acrylate-co-methacrylate), polyureas, and mixtures thereof.

The present invention further also relates to a coating composition obtained by mixing the first and second component of the two-component coating system just prior to application of the coating composition, whereby the coating composition comprises aziridinyl groups Q and carboxylic acid groups in an amount such that the stoichiometric amount (SA) of aziridinyl groups Q on carboxylic acid groups is preferably from 0.1 to 2.0, more preferably from 0.2 to 1.5, even more preferably from 0.25 to 0.95, most preferably from 0.3 to 0.8. The pH of the coating composition is preferably at least 7.5, more preferably at least 8, more preferably at least 8.5 and even more preferably at least 9.

The present invention further relates to a substrate having a coating obtained by (i) applying a coating composition as described above to a substrate and (ii) drying the coating composition by evaporation of volatiles. The drying of the coating composition is preferably affected at a temperature lower than 160° C., preferably at a temperature lower than 90° C., more preferably at a temperature lower than 50° C. and most preferably at ambient temperature. The coating composition according to the invention can be applied to any kind of substrate, such as for example wood, leather, concrete, textile, plastic, vinyl floors, glass, metal, ceramics, paper, wood plastic composite, glass fiber reinforced materials. The thickness of the dry coating on the substrate is preferably from 1 to 200 micron, more preferably from 5 to 150 micron and most preferably from 15 to 90 microns. In case the coating composition is an ink composition, the thickness of the dry ink is preferably from 0.005 to 35 micron, more preferably from 0.05 to 25 micron and most preferably from 4 to 15 microns.

A further aspect of the present invention is a multi-aziridine compound having:

a) from 2 to 6 of the following structural units (A):

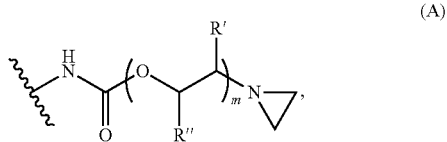

whereby
m is an integer from 1 to 6, preferably m is 1; and
R' and R" are both H, b) one or more connecting groups wherein each one of these connecting groups connects two of the structural units A and wherein the connecting groups consist of (i) at least two aliphatic hydrocarbon functionality or at least two cycloaliphatic hydrocarbon functionality and (ii) an isocyanurate functionality or an iminooxadiazinedione functionality, and wherein a pendant group is present on a connecting group, whereby the pendant group has the following structural formula:

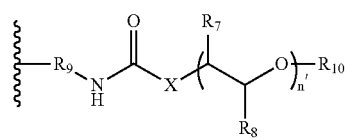

n' is the number of repeating units and is an integer from 1 to 50, preferably from 2 to 30, more preferably from 5 to 20, X is O or NH, preferably X is O, $R_7$ and $R_8$ are independently H or $CH_3$ in each repeating unit, $R_9$ is an aliphatic hydrocarbon group, preferably containing from 1 to 8 carbon atoms, or a cycloaliphatic hydrocarbon group, preferably containing from 4 to 10 carbon atoms, and $R_{10}$ contains at most 20 carbon atoms and is an aliphatic, cycloaliphatic or aromatic hydrocarbon group or a combination thereof, and c) a molecular weight in the range from 840 Daltons to 5000 Daltons.

The presence of the pendant group results in a decreased viscosity of the multi-aziridine compound and hence easier miscibility with the to be crosslinked polymer. In a preferred embodiment, one of $R_7$ and $R_8$ is H and the other $R_7$ or $R_8$ is $CH_3$. In another and more preferred embodiment, $R_7$ and $R_8$ are H. $R_{10}$ preferably is an aliphatic hydrocarbon group containing from 1 to 20 carbon atoms (preferably $CH_3$), a cycloaliphatic hydrocarbon group containing from 5 to 20 carbon atoms or an aromatic hydrocarbon group containing from 6 to 20 carbon atoms. Said multi-aziridine compound preferably contains 2 structural units, and the connecting group preferably consists of the array of the following consecutive functionalities: a first cycloaliphatic hydrocarbon functionality, an isocyanurate functionality or an iminooxadiazinedione functionality, and a second cycloaliphatic hydrocarbon functionality, and $R_9$ is a cycloaliphatic hydrocarbon group, whereby the first and second cycloaliphatic hydrocarbon functionality and $R_9$ are identical, more preferably the connecting group consists of the array of the following consecutive functionalities: a first aliphatic hydrocarbon functionality, an isocyanurate functionality or an iminooxadiazinedione functionality, and a second aliphatic hydrocarbon functionality, and $R_9$ is an aliphatic hydrocarbon group, whereby the first and second aliphatic hydrocarbon functionality and $R_9$ are identical. Preferably said multi-aziridine compound contains polyoxyethylene (—O—CH2-CH2-)$_x$ group(s) and/or polyoxypropylene (—O—CHCH3-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. Preferably, the multi-aziridine compound contains polyoxyethylene (—O—CH2-CH2-)$_x$ group(s), preferably in an amount of at least 0.1 wt. %, more preferably at least 6 wt. %, more preferably at least 10 wt. % and preferably in an amount of less than 45 wt. %, more preferably less than 25 wt. % and most preferably less than 16 wt. %, relative to the multi-aziridine compound. A multi-aziridine compound containing polyoxyethylene (—O—CH2-CH2-)$_x$ group(s) is preferably the reaction product of at least compound (B), a polyisocyanate and alkoxy poly(ethyleneglycol) (preferably methoxy poly(ethyleneglycol) (MPEG)) and/or poly(ethyleneglycol). The reaction product can be obtained by reacting at least compound B with the following structural formula:

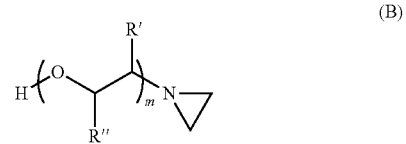

wherein R' and R" are as defined above, the polyisocyanate and alkoxy poly(ethyleneglycol) and/or poly(ethyleneglycol). The reaction product can also be obtained by reacting the polyisocyanate with alkoxy poly(ethyleneglycol) and/or poly(ethyleneglycol) and reacting the so-obtained compound with compound (B). The reaction product can also be obtained by reacting compound B with the polyisocyanate and reacting the so-obtained compound with alkoxy poly(ethyleneglycol) and/or poly(ethyleneglycol). The amount of alkoxy poly(ethyleneglycol) (preferably methoxy poly(ethyleneglycol) (MPEG)) and/or poly(ethyleneglycol) (PEG) chains with an average molecular weight higher than 2200 Daltons, preferably with an average molecular weight higher than 1600 Daltons in the multi-aziridine compound as defined above is preferably less than 35 wt. %, more preferably less than 15 wt. %, more preferably less than 5 wt. % and most preferably 0 wt. %. The methoxy poly(ethyleneglycol) (MPEG) and/or poly(ethyleneglycol) (PEG)

chains present in the multi-aziridine compound preferably have an average molecular weight lower than 1100 Daltons, more preferably lower than 770 Daltons and most preferably lower than 570 Daltons. The average molecular weight is determined by multiplying the OH functionality of the polyol by the equivalent weight of the polyol. The OH functionality of the polyol is given by the supplier of the polyol. In case the polyol is a diol, the OH functionality is 2. The equivalent weight of the polyol is calculated by dividing 56100 by the OH number of the polyol. The OH number of the polyol is measured by titration a known mass of polyol according to ISO 14900 (2017) and is expressed as mg KOH/g polyol.

The present invention is now illustrated by reference to the following examples. Unless otherwise specified, all parts, percentages and ratios are on a weight basis.

AV Determination

The acid value on solid material (AV) of a sample is determined based on the ASTM D1639-90(1996)e1 standard. In the procedure, the sample, dissolved in a good solvent, is titrated with alcoholic potassium hydroxide solution of a known concentration (KOH). The difference in titration volume between the sample and a blank is the measure of the acid value on solids, according to the following formula: $AV=[(Vblank-Vsample)*N_{KOH}*56.1]/(W*S/100)$, where AV is acid number on solids in mg KOH/g solid material, Vblank is the volume of KOH solution used in the blank, Vsample is the volume of KOH solution used in the sample, $N_{KOH}$ is the normality of the KOH solution, W is the sample weight in grams and S is the solids content of the sample in %. Measurements are performed in duplicate using a potentiometric endpoint on a Metrohm 702SM Titrino titrator (accepting the measurement if the difference between duplicates is <0.1 mg KOH/g solid material).

Chemical Resistance

Chemical resistance testing based on DIN 68861-1:2011-01 standard.

Unless indicated otherwise the chemical resistance is tested as follows:

Coating compositions are composed at 0.9 stoichiometric amounts (SA) of total carboxylic acid-reactive functional groups (e.g. aziridine) compared to carboxylic acid functional groups. Coating compositions are treated as described in the examples, and then cast at 100 μm wet layer thickness using a wire bar applicator. After casting, films were dried for 1 hour at 25° C., then annealed at 50° C. for 16 hours. Subsequently, a piece of cotton wool was soaked in 1:1 Ethanol:demineralized water (by weight) and placed on the film for 60 minutes (unless indicated otherwise). After removal of the cotton wool and overnight recovery, the spots were scored according to the following ranks:

1 Complete coating degradation
 2 Structural damage to the coating
 3 Severe marking on coating, visible from multiple directions
 4 Slight marking on coating, visible from specific angles
 5 No observed marking or gloss change Viscosity Measurements:

The apparent viscosity is determined according to ISO 2555:2018. The measurement is performed at 23° C. on a Brookfield DVE-LV viscometer (single-cylinder geometry) at 60 rpm. The spindle is selected from S62, S63 or S64, using the lowest numbered spindle (i.e. the largest spindle) that yields a reading between 10% and 100% torque.

Low Molecular Weight Fraction by LC-MS

LC system: Agilent 1290 Infinity II; Detector #1: Agilent 1290 Infinity II PDA; Detector #2: Agilent iFunnel 6550 Q-TOF-MS.

LC-MS analysis for the low molecular weight fraction was performed using the following procedure. A solution of ~100 mg/kg of material was prepared gravimetrically in methanol and stirred. 0.5 μl of this solution was injected into a UPLC equipped with ESI-TOF-MS detection. The column used was a 100×2.1 mm, 1.8 um, Waters HSS T3 C18 operated at 40° C. Flow rate was 0.5 ml·min$^{-1}$. Solvents used were 10 mM $NH_4CH_3COO$ in water set to pH 9.0 with $NH_3$ (Eluent A), Acetonitrile (B) and THF (C). Two binary gradients were applied from 80/20 A/B to 1/99 A/B in 10 minutes and from 1/99 A/B to 1/49/50 A/B/C in 5 minutes, after which starting conditions are applied (80/20 A/B). Assuming linear MS response of all components over all response ranges and an equal ionization efficiency for all components, Total Ion Current signals were integrated. In case of coelution extracted ion chromatograms of that particular species were integrated. Dividing the integrated signal of a particular low-molecular weight peak by the total integrated sample signal yields the fraction of that low molecular weight species.

MALDI-ToF-MS

All MALDI-ToF-MS spectra were acquired using a Bruker Ultraflextreme MALDI-ToF mass spectrometer. The instrument is equipped with a Nd:YAG laser emitting at 1064 nm and a collision cell (not used for these samples). Spectra were acquired in the positive-ion mode using the reflectron, using the highest resolution mode providing accurate masses (range 60-7000 m/z). Cesium Tri-iodide (range 0.3-3.5 kDa) was used for mass calibration (calibration method: IAV Molecular Characterisation, code MC-MS-05). The laser energy was 20%. The samples were dissolved in THF at approx. 50 mg/mL. The matrix used was: DCTB (trans-2-[3-(4-tert-Butylphenyl)-2-methyl-2-propenylidene]malononitrile), CAS Number 300364-84-5. The matrix solution was prepared by dissolving 20 mg in 1 mL of THF.

Sodium iodide was used as salt (NaI, CAS Number 7681-82-5); 10 mg was dissolved in 1 ml THF with a drop of MeOH added. Ratio sample:matrix:salt=10:200:10 (μl), after mixing, 0.5 μL was spot on MALDI plate and allowed to air-dry. The peaks measured in the MALDI spectrum are sodium adducts of multi-aziridine compounds, and in the context of this specification the molecular weight (MW) of the multi-aziridine compound corresponds to MW=Obs. $[M+M_{cation}]-M_{cation}$, where Obs. $[M+M_{cation}]$ is the MALDI-TOF MS peak and $M_{cation}$ is the exact mass of the cation used for making the adduct (in this case sodium with $M_{cation}$=23.0 Da). Multi-aziridine compounds can be identified by comparing the MW with the exact molecular mass (i.e. the sum of the—non-isotopically averaged—atomic masses of its constituent atoms) of a theoretical structure, using a maximum deviation of 0.6 Da.

Synthesis of P1, a Waterborne Polyurethane

A one-liter flask (equipped with a thermometer and an overhead stirrer), was charged with 29.9 grams of dimethylol propionic acid, 282.1 grams of a polypropylene glycol with a calculated average molecular weight (M) of 2000 Da and an OH-value of 56±2 mg KOH/g polypropylene glycol), 166.5 grams of a polypropylene glycol with a calculated average molecular weight (M) of 1000 Da and an OH-value of 112±2 mg KOH/g polypropylene glycol, and 262.8 grams of isophorone diisocyanate (the average molecular weight of each of the polyols is calculated from its OH-value according to the equation: M=2*56100/[OH-value in mg KOH/g polypropylene glycol). The reaction mixture was placed under N$_2$ atmosphere, heated to 50° C. and subsequently 0.07 g dibutyltin dilaurate were added to the reaction mixture. An exothermic reaction was observed; however proper care was taken in order for the reaction temperature not to exceed 97° C. The reaction was maintained at 95° C. for an hour. The NCO content of the resultant polyurethane P1' was 7.00% on solids as determined according to the ISO 14896 Method A (year 2009) (theoretically 7.44%) and the acid value of the polyurethane P1' was 16.1±1 mg KOH/g polyurethane P1'. The polyurethane P1' was cooled down to 60° C. and 18.7 grams of triethylamine were added, and the resulting mixture was stirred for 30 minutes. Subsequently, an aqueous dispersion of the polyurethane P1' (the aqueous dispersion of the polyurethane P1' is further referred to as P1) was prepared as follows: the thus prepared mixture of the polyurethane P1' and triethylamine was fed—at room temperature over a time period of 60 minutes—to a mixture of 1100 grams of demineralized water, 19.5 grams of nonylphenol ethoxylate (9 ethoxylate groups), and 4.0 grams of triethylamine. After the feed was completed, the mixture was stirred for additional 5 minutes, and subsequently 111.2 grams of hydrazine (16 wt % solution in water) were added to the mixture. The aqueous dispersion of the polyurethane P1' thus prepared was stirred for an additional 1 h and P1 was obtained.

PREPARATIVE EXAMPLE 2: SYNTHESIS OF WATERBORNE ACRYLIC POLYMER A1

A 2 L four-necked flask equipped with a thermometer and overhead stirrer was charged with sodium lauryl sulphate (30% solids in water, 18.6 grams of solution) and demineralized water (711 grams). The reactor phase was placed under N$_2$ atmosphere and heated to 82° C. A mixture of demineralized water (112 grams), sodium lauryl sulphate (30% solids in water, 37.2 grams of solution), methyl methacrylate (209.3 grams), n-butyl acrylate (453.56 grams) and methacrylic acid (34.88 grams) was placed in a large feeding funnel and emulsified with an overhead stirrer (monomer feed). Ammonium persulphate (1.75 grams) was dissolved in demineralized water (89.61 grams) and placed in a small feeding funnel (initiator feed). Ammonium persulphate (1.75 grams) was dissolved in demineralized water (10.5 grams), and this solution was added to the reactor phase. Immediately afterwards, 5% by volume of the monomer feed was added to the reactor phase. The reaction mixture then exothermed to 85° C. and was kept at 85° C. for 5 minutes. Then, the residual monomer feed and the initiator feed were fed to the reaction mixture over 90 minutes, maintaining a temperature of 85° C. After completion of the feeds, the monomer feed funnel was rinsed with demineralized water (18.9 grams) and reaction temperature maintained at 85° C. for 45 minutes. Subsequently, the mixture was cooled to room temperature and brought to pH=7.2 with ammonia solution (6.25 wt. % in demineralized water), and brought to 40% solids with further demineralized water.

Genotoxicity Testing

Genotoxicity of examples and comparatives was evaluated by the ToxTracker® assay (Toxys, Leiden, the Netherlands). The ToxTracker assay is a panel of several validated Green Fluorescent Protein (GFP)-based mouse embryonic stem (mES) reporter cell lines that can be used to identify the biological reactivity and potential carcinogenic properties of newly developed compounds in a single test. This methodology uses a two step-approach.

In the first step a dose range finding was performed using wild-type mES cells (strain B4418). 20 different concentrations for each compound was tested, starting at 10 mM in DMSO as highest concentration and nineteen consecutive 2-fold dilutions.

Next, genotoxicity of examples and comparatives was evaluated using specific genes linked to reporter genes for the detection of DNA damage; i.e. Bscl2 (as elucidated by U.S. Pat. No. 9,695,481B2 and EP2616484B1) and Rtkn (Hendriks et. al. Toxicol. Sci. 2015, 150, 190-203) biomarkers.

Genotoxicity was evaluated at 10, 25 and 50% cytotoxicity in absence and presence of rat S9 liver extract-based metabolizing systems (aroclor1254-induced rats, Moltox, Boone, NC, USA). The independent cell lines were seeded in 96-well cell culture plates, 24 h after seeding the cells in the 96-well plates, fresh ES cell medium containing the diluted test substance was added to the cells. For each tested compound, five concentrations are tested in 2-fold dilutions. The highest sample concentration will induce significant cytotoxicity (50-70%). In case of no or low cytotoxicity, 10 mM or the maximum soluble mixture concentration is used as maximum test concentration. Cytotoxicity is determined by cell count after 24 h exposure using a Guava easyCyte 10HT flow cytometer (Millipore).

GFP reporter induction is always compared to a vehicle control treatment. DMSO concentration is similar in all wells for a particular compound and never exceeds 1%. All compounds were tested in at least three completely independent repeat experiments. Positive reference treatment with cisplatin (DNA damage) were included in all experiments. Metabolic was evaluated by addition of S9 liver extract. Cells are exposed to five concentrations of the test compound in the presence of S9 and required co-factors (RegenSysA+B, Moltox, Boone, NC, USA) for 3 h. After washing, cells are incubated for 24 h in fresh ES cell medium. Induction of the GFP reporters is determined after 24 h exposure using a Guava easyCyte 10HT flow cytometer (Millipore). Only GFP expression in intact single cells is determined. Mean GFP fluorescence and cell concentrations in each well is measured, which is used for cytotoxicity assessment. Data was analyzed using ToxPlot software (Toxys, Leiden, the Netherlands). The induction levels reported are at compound concentrations that induce 10%, 25% and 50% cytotoxicity after 3 h exposure in the presence of S9 rat liver extract and 24 h recovery or alternatively after 24 h exposure when not in the presence of S9 rat liver extract.

A positive induction level of the biomarkers is defined as equal to or higher than a 2-fold induction at at least one of 10, 25 and 50% cytotoxicity in the absence or presence of the metabolizing system rat S9 liver extract; a weakly positive induction as higher than 1.5-fold and lower than 2-fold induction at at least one of 10, 25 and 50% cytotoxicity (but lower than 2-fold at 10, 25 and 50% cytotoxicity) in the absence or presence of the metabolizing system rat S9 liver extract and a negative as lower than or equal to a 1.5-fold induction at 10, 25 and 50% cytotoxicity in the absence and presence of rat S9 liver extract-based metabolizing systems.

Components and Abbreviations Used:

Dimethylformamide (CAS No. 68-12-2) was obtained from Acros Organics (a division of Thermo Fisher Scientific).

Di(propylene glycol) dimethyl ether (Proglyde DMM, CAS No. 111109-77-4) was obtained from Dow Inc Trimethylolpropane tris(2-methyl-1-aziridinepropionate), CAS No. 64265-57-2, CX-100 was obtained from DSM.

Pentaerythritol tris(3-(1-aziridinyl)propionate), CAS number 57116-45-7 was obtained from ABCR.
IPDI (5-isocyanato-1-(isocyanatomethyl)-1,3,3-trimethylcyclohexane, Desmodur® I, isophorone diisocyanate, CAS No. 4098-71-9) was obtained from Covestro.
Polyethylene Glycol Monomethyl Ether (CAS No. 9004-74-4) with a number average molecular weight of 1000 Da was obtained from Tokyo Chemical Industry Co., Ltd.
Vestanat® T 1890/100, an isophorone diisocyanate based isocyanurate (CAS No. 67873-91-0) was obtained from Evonik.
Desmodur® N3600 was obtained from Covestro.
1-methoxy-2-propanol acetate (propylene glycol methyl ether acetate, CAS No. 108-65-6) was obtained from Shell Chemicals.
1-(2-hydroxyethyl)ethyleneimine) (CAS No. 1072-52-2) was obtained from Tokyo Chemical Industry Co., Ltd.
Jeffamine® XTJ-436 (CAS No. 118270-87-4) was obtained from Huntsman
Bismuth neodecanoate (CAS No. 34364-26-6) obtained from TIB chemicals AG (Mannheim, Germany).
Hydrazine (16% solution in water, CAS No. 302-01-2) was obtained from Honeywell.
Dimethylol propionic acid (DMPA, CAS No. 4767-03-7) was obtained from Perstop Polyols.
Triethylamine (TEA, CAS No. 121-44-8) was obtained from Arkema
1-propanol (CAS No. 71-23-8) was obtained from Sigma-Aldrich.
Tin 2-ethylhexanoate (CAS No. 301-10-0) was obtained from Sigma-Aldrich.
Dibutyltindilaurate (CAS No. 77-58-7) was obtained from Sigma-Aldrich.
Tegomer® D3403 was obtained from Evonik.
Polypropyleneglycol with a number average molecular weight of 1000 Da and with a number average molecular weight of 2000 Da was obtained from BASF.
3-Methyl-1-phenyl-2-phospholene-1-oxide (CAS No. 707-61-9) was obtained from Sigma-Aldrich.
1-Butanol (CAS No. 71-36-3) was obtained from Sigma-Aldrich.
Sodium lauryl sulphate (30% solution in water, CAS No. 73296-89-6) was obtained from BASF.
Methyl methacrylate (CAS No. 80-62-6) was obtained from Lucite Int.
n-Butyl acrylate (CAS No. 141-32-2) was obtained from Dow Chemical.
Methacrylic acid (CAS No. 79-41-4) was obtained from Lucite Int.
Ammonium persulphate (CAS No. 7727-54-0) was obtained from United Initiators.
Ammonia (25% solution in water, CAS No. 1336-21-6) was obtained from Merck

COMPARATIVE EXAMPLE 1

Comparative Example 1 is trimethylolpropane tris(2-methyl-1-aziridinepropionate), CAS number 64265-57-2 obtained from DSM. Chemical structure is shown below.

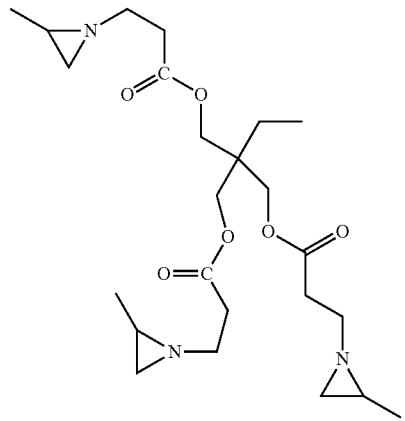

For reference, the performance of trimethylolpropane tris(2-methyl-1-aziridinepropionate) as a crosslinker was assessed using spot tests on coating surfaces, based on procedures from the DIN 68861-1:2011-01 standard. For these tests, 0.23 parts of the compound were mixed with 0.60 parts of Proglyde™ DMM (dipropylene glycol dimethyl ether, mixture of isomers) and incubated at 80° C. for 10 minutes under regular agitation. Subsequently, 0.56 parts of the resulting solution were added to 20 parts of P1 under continuous stirring, and the resulting mixture was further stirred for 30 minutes. Afterwards, this coating composition was filtered and applied to Leneta test cards using 100 μm wire rod applicators (Test C1-1). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

Ethanol Spot Test

|  | Sample | | | |
| --- | --- | --- | --- | --- |
|  | 30 min | 60 min | 120 min | 300 min |
| Test C1-1 | 4 | 4 | 3 | 3 |

Genotoxicity Test

|  | Without S9 rat liver extract | | | | | | With S9 rat liver extract | | | | | |
| --- | --- | --- | --- | --- | --- | --- | --- | --- | --- | --- | --- | --- |
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Comp. Ex. 1 | 1.2 | 1.5 | 2.0 | 1.4 | 2.0 | 3.2 | 1.7 | 2.3 | 2.1 | 3.0 | 4.3 | 3.4 |

The genotoxicity test results shows that the crosslinker of Comparative Example 1 is genotoxic.

EXAMPLE 1

3.83 grams of 1-(2-hydroxyethyl)ethyleneimine) (Cas No. 1072-52-2, obtained from Tokyo Chemical Industry), 12.21 grams of a poly(ethylene glycol) monomethyl ether with an average Mn of 1000 Da and 126 grams of dimethylformamide were charged to a reaction flask equipped with a thermometer. The mixture was stirred with a mechanical upper stirrer under a nitrogen atmosphere and heated to 50° C., after which 0.12 grams of bismuth neodecanoate was added to the flask and a mixture of 15.00 grams of Vestanat® T 1890/100 in 63 grams of dimethylformamide was fed in 30 minutes to a reaction flask. After this, the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.36 grams of 1-butanol were added to the mixture, followed by further reaction to complete disappearance the aforementioned NCO-stretch peak. The solvent was removed in vacuo to obtain an opaque waxy solid. The calculated molecular weights of the theoretical main components were 927.62 Da (three aziridines), 1797.12 (two aziridines, 21 EG repeating units) and 1841.15 Da (two aziridines, 22 EG repeating units) chemical structures are shown below.

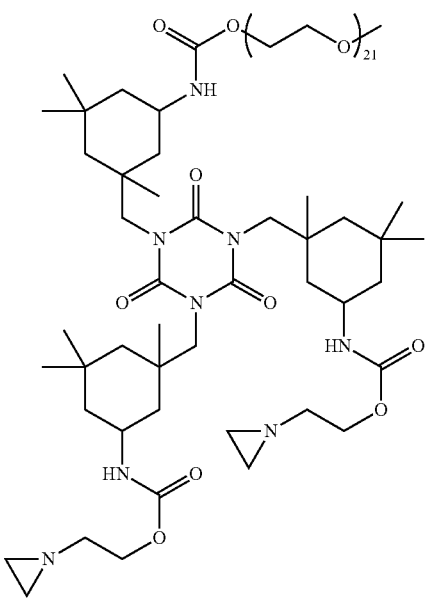

Molecular weight was confirmed by Maldi-TOF-MS: Calcd. [M+Na+]=1820.12 Da; Obs. [M+Na+]=1820.15 Da.

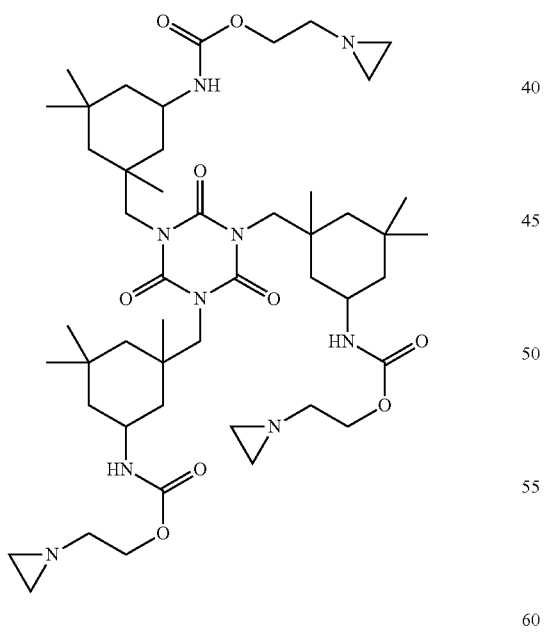

Molecular weight was confirmed by Maldi-TOF-MS: Calcd. [M+Na+]=950.62 Da; Obs. [M+Na+]=950.52 Da.

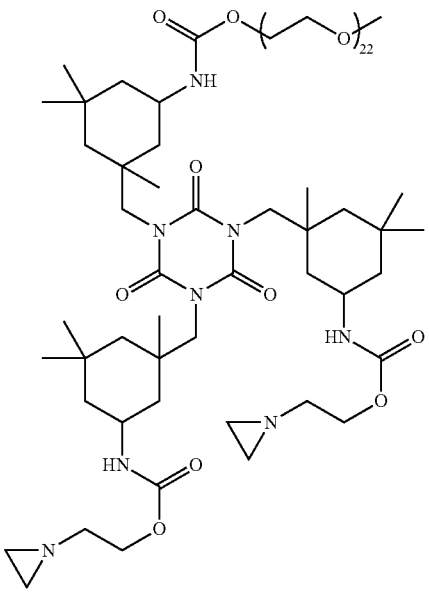

Molecular weight was confirmed by Maldi-TOF-MS: Calcd. [M+Na+]=1864.15 Da; Obs. [M+Na+]=1864.20 Da.

The following components with a mass below 820 Da were detected by LC-MS and quantified:

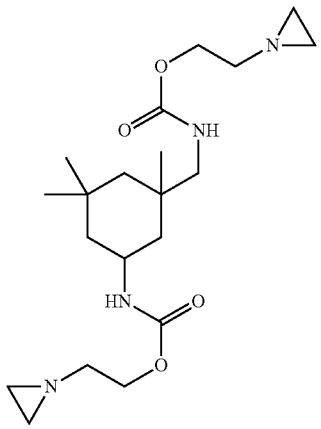 [SMILES: CC1(C)CC(NC(=O)OCCN2CC2)CC(C)(CNC(=O)OCCN2CC2)C1]

was present in the composition at 0.04 wt %
Performance of the synthesized compound as a crosslinker was assessed using spot tests on coating surfaces, based on procedures from the DIN 68861-1:2011-01 standard. For these tests, 0.75 parts of the composition were mixed with 0.75 parts of 1-methoxy-2-propyl acetate and incubated at 80° C. for 10 minutes under regular agitation. Subsequently, 1.5 parts of the resulting solution were added to 10 parts of P1 under continuous stirring, and the resulting mixture was further stirred for 30 minutes. Afterwards, this coating composition was filtered and applied to Leneta test cards using 100 μm wire rod applicators (Test 1-1). For reference, films were also cast from the same composition lacking a crosslinker (Test 1-2). The films were dried for 16 hours at 25° C., then annealed at 50° C. for 1 hour and further dried fo 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

Ethanol Spot Test

|  | Sample | |
|---|---|---|
|  | 30 min | 240 min |
| Test 1-1 | 4 | 4 |
| Test 1-2 | 1 | 1 |

For further performance tests, 1.0 parts of the composition were mixed with 1.0 parts of 1-methoxy-2-propyl acetate and incubated at 80° C. for 10 minutes under regular agitation. Subsequently, 1.5 parts of the resulting solution were added to 10.5 parts of A1 under continuous stirring, and the resulting mixture was further stirred for 30 minutes. Afterwards, this coating composition was filtered and applied to Leneta test cards using 100 μm wire rod applicators (Test 1-3). For reference, films were also cast from the same composition lacking a crosslinker (Blank 1-4). The films were dried for 16 hours at 25° C., then annealed at 50° C. for 1 hour and further dried for 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

|  | Sample | |
|---|---|---|
|  | 60 min | 240 min |
| Test 1-3 | 3 | 3 |
| Blank 1-4 | 1 | 1 |

Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Ex. 1 | 1.2 | 1.3 | 1.3 | 1.2 | 1.1 | 1.0 | 1.2 | 1.3 | 1.3 | 1.3 | 1.1 | 1.3 |

The genotoxicity test results show that the crosslinker composition of Example 1 is non-genotoxic.

COMPARATIVE EXAMPLE 2

15.0 grams of Desmodur N 3600 and 75 grams of dimethylformamide were charged to a reaction flask equipped with a thermometer. The mixture was stirred with a mechanical upper stirrer under a nitrogen atmosphere. The mixture was than heated to 50° C., whereafter 6.80 grams of 1-(2-hydroxyethyl)ethyleneimine was added. 15 minutes later 0.03 grams of bismuth neodecanoate was charged to the reaction flask, which was then heated further to 60° C. Samples were taken at regular intervals and the reaction progress was monitored using a Bruker Alpha FT-IR spectrometer until no NCO-stretch at 2200-2300 $cm^{-1}$ was observed. The solvent was removed in vacuo to obtain a clear, slightly yellowish highly viscous liquid. The calculated molecular weight of the theoretical main component was 765.47 Da, chemical structure is shown below.

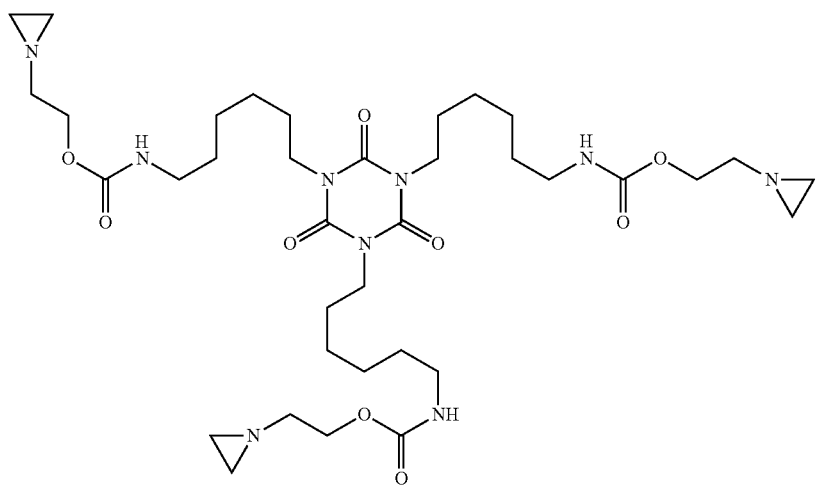

Molecular weight was confirmed by Maldi-TOF-MS: Calcd. [M+K+]=804.43 Da; Obs. [M+K+]=804.27 Da.

Genotoxicity Test

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Comp. Ex. 2 | 1.1 | 1.3 | 1.4 | 1.7 | 2.4 | 2.8 | 1.4 | 1.9 | 1.9 | 2.0 | 3.4 | 3.0 |

The genotoxicity test results show that the reaction product of Comp Ex 2 is genotoxic.

EXAMPLE 2

3.83 grams of 1-(2-hydroxyethyl)ethyleneimine) (Cas No. 1072-52-2, obtained from Tokyo Chemical Industry), 12.27 grams of Jeffamine® XTJ-436 (CAS number 118270-87-4, obtained from Huntsman) and 126 grams of dimethylformamide were charged to a reaction flask equipped with a thermometer. The mixture was stirred with a mechanical upper stirrer under a nitrogen atmosphere and heated to 50° C., after which 0.10 grams of bismuth neodecanoate was added to the flask and a mixture of 15.00 grams of Vestanat® T 1890/100 in 95 grams of dimethylformamide was fed in 30 minutes to a reaction flask. After this, the mixture was heated further to 80° C. Samples were taken at regular intervals and the reaction progress was monitored using a Bruker Alpha FT-IR spectrometer until no change in NCO-stretch at 2200-2300 cm$^{-1}$ was observed. Subsequently, 0.36 grams of 1-butanol were added to the mixture, followed by further reaction to complete disappearance the aforementioned NCO-stretch peak. The solvent was removed in vacuo to obtain an opaque waxy solid. The calculated molecular weights of the theoretical main components were 927.62 Da (three aziridines), 1814.29 Da (two aziridines, 13 PO repeating units) and 1827.33 Da (two aziridines, 14PO repeating units) chemical structures are shown below.

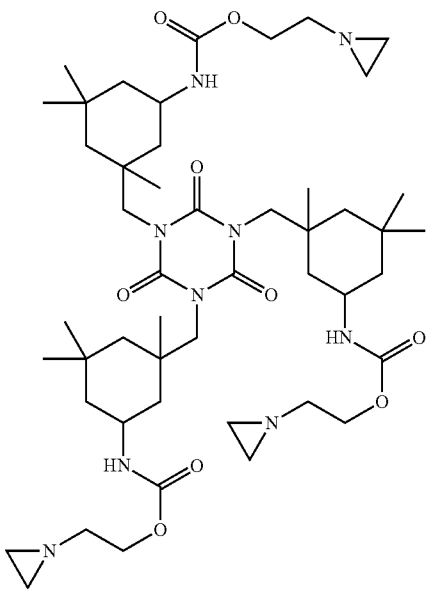

Molecular weight was confirmed by Maldi-TOF-MS: Calcd. [M+Na+]=950.62 Da; Obs. [M+Na+]=950.52 Da.

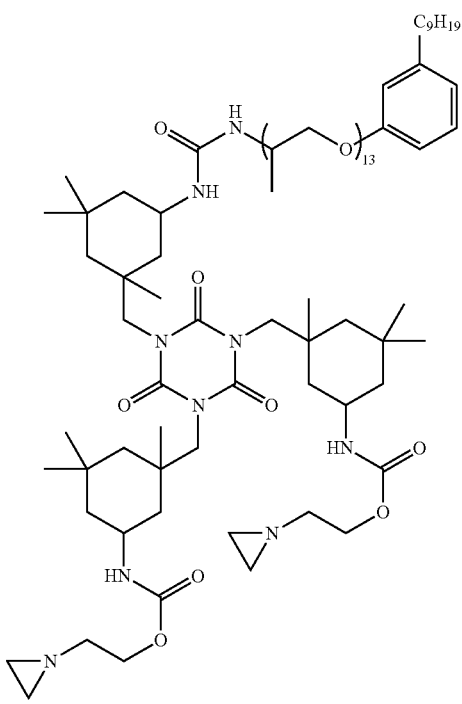

Molecular weight was confirmed by Maldi-TOF-MS: Calcd. [M+Na+]=1837.28 Da; Obs. [M+Na+]=1837.15 Da.

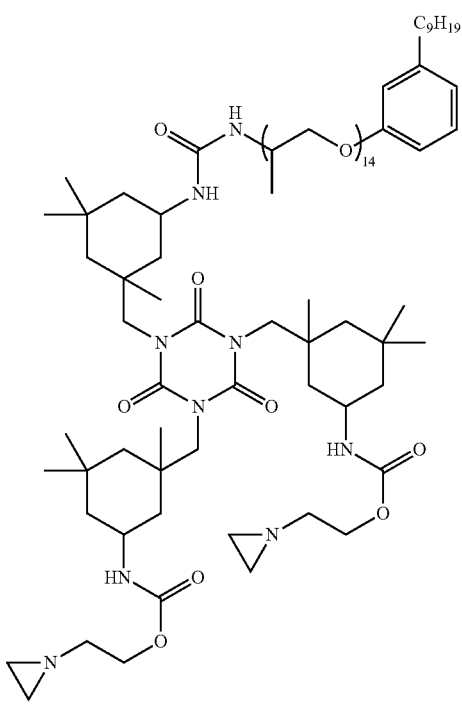

Molecular weight was confirmed by Maldi-TOF-MS: Calcd. [M+Na+]=1895.32 Da; Obs. [M+Na+]=1895.15 Da.

The following components with a mass below 820 Da were detected by LC-MS and quantified:

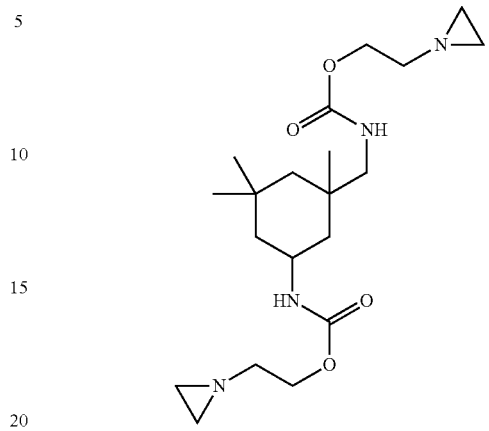

was present in the composition at 0.10 wt %.

Performance of the synthesized compound as a crosslinker was assessed using spot tests on coating surfaces, based on procedures from the DIN 68861-1:2011-01 standard. For these tests, 1.03 parts of the composition were mixed with 0.26 parts of dimethylformamide and incubated at 80° C. for 10 minutes under regular agitation. Subsequently, 1.29 parts of the resulting solution were added to 15 parts of P1 under continuous stirring, and the resulting mixture was further stirred for 30 minutes. Afterwards, this coating composition was filtered and applied to Leneta test cards using 100 μm wire rod applicators (Test 2-1). For reference, films were also cast from the same composition lacking a crosslinker (Test 2-2). The films were dried for 16 hours at 25° C., then annealed at 50° C. for 1 hour and further dried fo 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

Ethanol Spot Test

|  | Sample | |
| --- | --- | --- |
|  | 30 min | 240 min |
| Test 2-1 | 4 | 3 |
| Test 2-2 | 1 | 1 |

For further performance tests, 1.45 parts of the composition were mixed with 0.39 parts of dimethylformamide and incubated at 80° C. for 10 minutes under regular agitation. Subsequently, 1.84 parts of the resulting solution were added to 10.5 parts of A1 under continuous stirring, and the resulting mixture was further stirred for 30 minutes. Afterwards, this coating composition was filtered and applied to Leneta test cards using 100 μm wire rod applicators (Test 2-3). For reference, films were also cast from the same composition lacking a crosslinker (Blank 2-4). The films were dried for 16 hours at 25° C., then annealed at 50° C. for 1 hour and further dried fo 24 hours at 25° C. Subsequently, a piece of cotton wool was soaked in 1:1 EtOH:demineralized water and placed on the film for various timespans. After removal of the EtOH and 60 minutes recovery, the following results were obtained (a score of 1 indicates complete degradation of the film, 5 indicates no damage visible):

| | Sample | |
|---|---|---|
| | 60 min | 240 min |
| Test 2-3 | 3 | 3 |
| Blank 2-4 | 1 | 1 |

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Ex. 2 | 1.2 | 1.5 | 1.6 | 1.4 | 1.3 | 1.2 | 1.1 | 1.6 | 1.7 | 1.4 | 1.3 | 1.2 |

The genotoxicity test results show that the crosslinker composition of Example 2 only has weakly positive induced genotoxicity.

COMPARATIVE EXAMPLE 3

Comparative Example 3 is pentaerythritol tris(3-(1-aziridinyl)propionate), CAS number 57116-45-7, obtained from ABCR. Chemical structure is shown below.

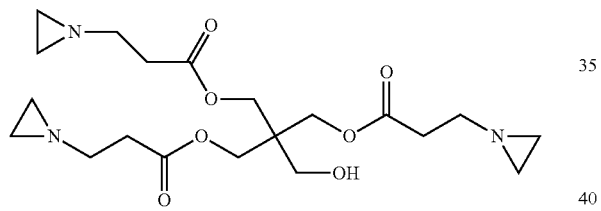

Genotoxicity Test

| | Without S9 rat liver extract | | | | | | With S9 rat liver extract | | | | | |
|---|---|---|---|---|---|---|---|---|---|---|---|---|
| | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Comp. Ex. 3 | 1.2 | 1.4 | 2.1 | 1.2 | 1.7 | 3.5 | 1.1 | 1.5 | 2.3 | 1.3 | 2.1 | 4.3 |

The genotoxicity test results show that the crosslinker of Comparative Example 3 is genotoxic.

COMPARATIVE EXAMPLE 4 (EXAMPLE 5 U.S. Pat. No. 5,258,481)

Under a nitrogen atmosphere, 21.3 g (0.354 mole) of 1-propanol was added over a period of 6 hours to 78.7 g Isophorone diisocyanate (IPDI) and 0.01 g tin 2-ethyl hexanoate at 20-25° C., while stirring. After standing overnight, 196.3 g (0.883 mole) IPDI, 74.1 g (0.0628 mole) Tegomer D3403 and 2.4 g 3-Methyl-1-phenyl-2-phospholene-1-oxide were added. The mixture was heated while stirring to 150° C. The mixture was kept at 150° C. until NCO content was 7.0 wt %. Mixture was cooled to 80° C. and 333 g methoxypropyl acetate was added. A solution of isocyanate functional polycarbodiimide was obtained with a solid content of 50.6 wt % and an NCO content of 7.0 wt % on solids.

To 100 g of this isocyanate functional polycarbodiimide was added 7.0 g 1-(2-hydroxyethyl)ethyleneimine (0.08 mole). One drop of dibutyltin dilaurate was added. The mixture was heated to 80° C. while stirring. The mixture was kept at 80° C. for 1 hour. FTIR showed a small remaining isocyanate signal, which disappeared after a few days. The solution was further diluted with 8.0 g methoxypropyl acetate, resulting in a yellow solution with a solid content of 50.4 wt %. This aziridine functional carbodiimide contains 3.2 meq acid reactive groups (i.e aziridine and carbodiimide functionality) per gram solids. The generalized structure of this carbodiimide is depicted below.

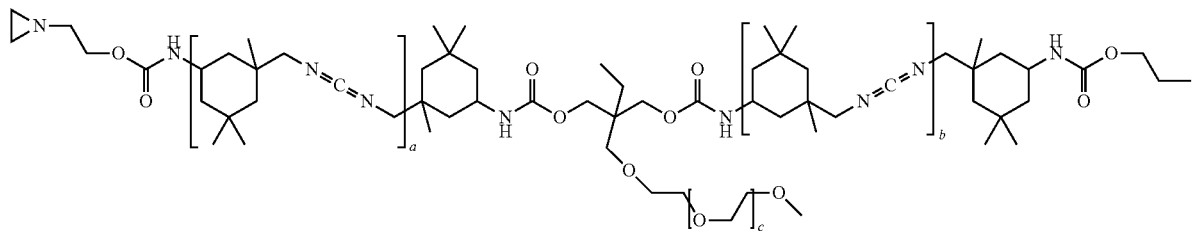

in which a, b and c indicates repeating units.
This generalized structure was confirmed by MALDI-TOF-MS, an example is shown below:

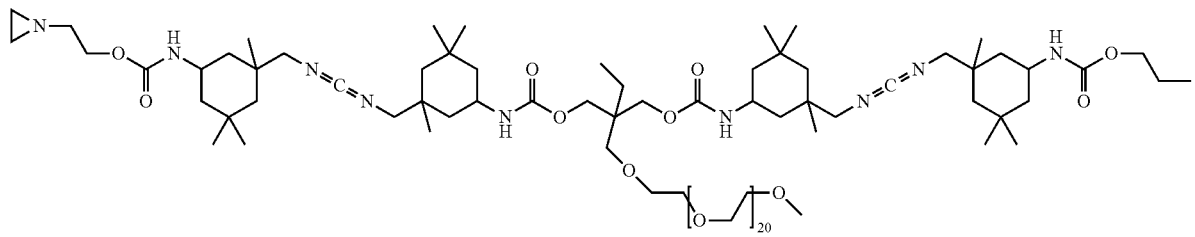

Molecular weight was confirmed by Maldi-TOF-MS: Calcd. [M+Na+]=2043.34 Da; Obs. [M+Na+]=2043.32 Da.

Genotoxicity Test Results:

|  | Without S9 rat liver extract | | | | | | With S9 rat liver extract | | | | | |
|---|---|---|---|---|---|---|---|---|---|---|---|---|
|  | Bscl 2 | | | Rtkn | | | Bscl 2 | | | Rtkn | | |
| concentration → | 10 | 25 | 50 | 10 | 25 | 50 | 10 | 25 | 50 | 10 | 25 | 50 |
| Comp. Ex. 4 | 1.3 | 1.5 | 1.6 | 1.2 | 1.9 | 1.9 | 1.2 | 1.4 | 1.5 | 2.0 | 2.0 | 1.8 |

The genotoxicity test results demonstrate that the crosslinker of comparative example 4 is genotoxic.

The invention claimed is:

1. A two-component coating system comprising a first component and a second component each of which is separate and distinct from each other, wherein
the first component comprises a carboxylic acid functional polymer dissolved and/or dispersed in an aqueous medium, whereby the carboxylic acid functional polymer contains carboxylic acid groups and/or carboxylate groups, and
the second component comprises a multi-aziridine compound having:
a) from 2 to 6 of the following structural units (A):

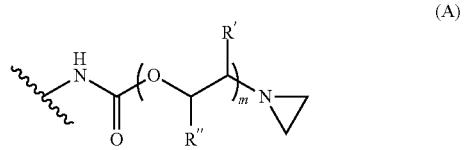

whereby
m is an integer from 1 to 6, and
R' and R" are both H;

b) one or more linking chains wherein each one of these linking chains links two of the structural units A, whereby a linking chain is the shortest chain of consecutive atoms that links two structural units A;

c) one or more connecting groups whereby each one of the connecting groups connects two of the structural units A and whereby the connecting groups consist of (i) at least two aliphatic hydrocarbon functionality or at least two cycloaliphatic hydrocarbon functionality and (ii) an isocyanurate functionality or an iminooxadiazinedione functionality,
and
wherein a pendant group is present on a connecting group, whereby the pendant group has the following structural formula:

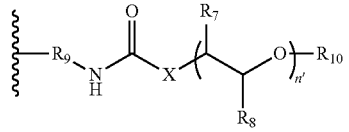

n' is the number of repeating units and is an integer from 1 to 50,
X is O or NH,
$R_7$ and $R_8$ are independently H or $CH_3$ in each repeating unit,
$R_9$ is an aliphatic hydrocarbon group, or a cycloaliphatic hydrocarbon group and $R_{10}$ contains at most 20 carbon atoms and is an aliphatic, cycloaliphatic or aromatic hydrocarbon group or a combination thereof; and d) a molecular weight in the range from 840 Daltons to 5000 Daltons, wherein the molecular weight is determined using MALDI-TOF mass spectrometry.

2. The two-component coating system according to claim 1, wherein m is 1.

3. The two-component coating system according to claim 1, wherein the multi-aziridine compound contains 2 or 3 structural units (A).

4. The two-component coating system according to claim 1, wherein the linking chains consist of from 4 to 300 atoms and the linking chains are a collection of atoms covalently connected which collection of atoms consists of i) carbon atoms, ii) carbon and nitrogen atoms, or iii) carbon, oxygen and nitrogen atoms.

5. The two-component coating system according to claim 1, wherein the number of consecutive C atoms and optionally O atoms between the N atom of the urethane group in a structural unit A and the next N atom which is either present in the linking chain or which is the N atom of the urethane group of another structural unit A is at most 9.

6. The two-component coating system according to claim 1, wherein the multi-aziridine compound has a molecular weight of from 840 to 3800 Daltons.

7. The two-component coating system according to claim 1, wherein X is O and $R_7$ and $R_8$ are H.

8. The two-component coating system according to claim 1, wherein the multi-aziridine compound contains 2 structural units (A).

9. The two-component coating system according to claim 8, wherein the connecting group consists of the array of the following consecutive functionalities: a first aliphatic hydrocarbon functionality, an isocyanurate functionality or an iminooxadiazinedione functionality, and a second aliphatic hydrocarbon functionality, and $R_9$ is an aliphatic hydrocarbon group, whereby the first and second aliphatic hydrocarbon functionality and $R_9$ are identical.

10. The two-component coating system according to claim 1, wherein the multi-aziridine compound contains polyoxyethylene (—O—CH2-CH2-)$_x$ group(s) in an amount of at least 0.1 wt. % and in an amount of less than 45 wt. % relative to the multi-aziridine compound.

11. The two-component coating system according to claim 1, wherein the multi-aziridine compound is obtained by reacting at least a polyisocyanate and a compound B with the following structural formula:

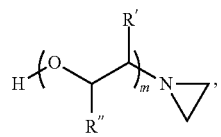

whereby the molar ratio of compound B to polyisocyanate is from 2 to 6.

12. The two-component coating system according to claim 11, wherein the polyisocyanate is a polyisocyanate with aliphatic reactivity in which all of the isocyanate groups are directly bonded to aliphatic or cycloaliphatic hydrocarbon groups, irrespective of whether aromatic hydrocarbon groups are also present.

13. The two-component coating system according to claim 1, wherein the second component is a crosslinker composition comprising at least one of the multi-aziridine compound and further comprising at least one additional component.

14. The two-component coating system according to claim 13, wherein the amount of aziridine functional molecules having a molecular weight lower than 820 Daltons is lower than 1.5 wt. % relative to the total weight of the crosslinker composition, whereby the molecular weight is determined using LC-MS, and wherein the crosslinker composition contains less than 5 wt. % of water.

15. A substrate having a coating obtained by (i) applying a coating composition obtained by mixing the first and second component of the two-component system according to claim 1 to a substrate and (ii) drying the coating composition by evaporation of volatiles.

16. A multi-aziridine compound having:
a) from 2 to 6 of the following structural units (A):

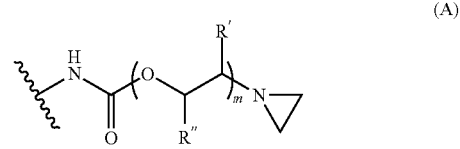

whereby
m is an integer from 1 to 6; and
R' and R" are both H, b) one or more linking chains wherein each one of these linking chains links two of the structural units A, whereby a linking chain is the shortest chain of consecutive atoms that link two structural units A;

c) one or more connecting groups wherein each one of these connecting groups connects two of the structural units A and wherein the connecting groups consist of (i) at least two aliphatic hydrocarbon functionality or at least two cycloaliphatic hydrocarbon functionality and (ii) an isocyanurate functionality or an iminooxadiazinedione functionality, and wherein a pendant group is present on a connecting group, whereby the pendant group has the following structural formula:

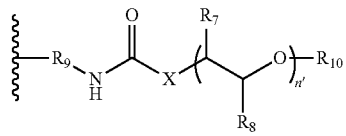

n' is the number of repeating units and is an integer from 1 to 50,
X is O or NH,
$R_7$ and $R_8$ are independently H or $CH_3$ in each repeating unit,
$R_9$ is an aliphatic hydrocarbon group or a cycloaliphatic hydrocarbon group and
$R_{10}$ contains at most 20 carbon atoms and is an aliphatic, cycloaliphatic or aromatic hydrocarbon group or a combination thereof, and d) a molecular weight in the range from 840 Daltons to 5000 Daltons, wherein the molecular weight is measured using MALDI-TOF mass spectrometry.

17. The multi-aziridine compound according to claim 16, wherein X is O and $R_7$ and $R_8$ are independently H.

18. The multi-aziridine compound according to claim 16, wherein the multi-aziridine compound contains 2 structural units (A).

19. The multi-aziridine compound according to claim 16, wherein the connecting group consists of the array of the 5 following consecutive functionalities: a first aliphatic hydrocarbon functionality, an isocyanurate functionality or an iminooxadiazinedione functionality, and a second aliphatic hydrocarbon functionality, and $R_9$ is an aliphatic hydrocarbon group, whereby the first and second aliphatic hydrocarbon functionality and $R_9$ are identical.

* * * * *